US012644159B2

(12) United States Patent
Eltzov et al.

(10) Patent No.: US 12,644,159 B2
(45) Date of Patent: Jun. 2, 2026

(54) DEVICE AND METHODS FOR DETECTING FUNGAL PATHOGENICITY IN POSTHARVEST PRODUCE

(71) Applicant: The State of Israel, Ministry of Agriculture & Rural Development, Agricultural Research Organization (ARO) (VOLCANI CENTER), Rishon Lezion (IL)

(72) Inventors: Evgeni Eltzov, Ashdod (IL); Noam Alkan, Kidron (IL)

(73) Assignee: The State of Israel, Ministry of Agriculture & Rural Development, Agricultural Research Organization (ARO) (Volcani institute), Rishon Lezion (IL)

( * ) Notice: Subject to any disclaimer, the term of this patent is extended or adjusted under 35 U.S.C. 154(b) by 909 days.

(21) Appl. No.: 17/783,718

(22) PCT Filed: Dec. 9, 2020

(86) PCT No.: PCT/IL2020/051272
§ 371 (c)(1),
(2) Date: Jun. 9, 2022

(87) PCT Pub. No.: WO2021/117040
PCT Pub. Date: Jun. 17, 2021

(65) Prior Publication Data
US 2023/0102388 A1     Mar. 30, 2023

Related U.S. Application Data

(60) Provisional application No. 62/945,238, filed on Dec. 9, 2019.

(51) Int. Cl.
*C12Q 1/6895* (2018.01)
*B01L 3/00* (2006.01)
(Continued)

(52) U.S. Cl.
CPC ...... *C12Q 1/6895* (2013.01); *B01L 3/502761* (2013.01); *C12Q 1/28* (2013.01);
(Continued)

(58) Field of Classification Search
None
See application file for complete search history.

(56) References Cited

U.S. PATENT DOCUMENTS 8,213,017 B2     7/2012     Wiki
2003/0143571 A1     7/2003     Sharp et al.
(Continued)

FOREIGN PATENT DOCUMENTS

CA       2460212 C     12/2003
CN       102944585 A     2/2013
(Continued)

OTHER PUBLICATIONS

Bilkiss, M, Shiddiky, M. J., & Ford, R. (2019). Advanced Diagnostic Approaches for Necrotrophic Fungal Pathogens of Temperate Legumes \Vith a Focus on *Botrytis* spp. Frontiers in microbiology, 10, 1889. (Year: 2019).*
(Continued)

*Primary Examiner* — Matthew D Krcha
(74) *Attorney, Agent, or Firm* — The Roy Gross Law Firm, LLC; Roy Gross

(57)     ABSTRACT

The present invention discloses a system and a method for detecting different developmental stages of fungi life cycle in postharvest crops. More particularly, the system comprises a measuring transducer, such as a CMOS photodetector and immobilized fungal nucleic acid strands. RNA from the tested postharvest produce sample is loaded onto the system of the present invention, and specific fungal mRNA transcripts anneal to the immobilized strands. A reporter strand conjugated to a signal-generating component
(Continued)

100 further binds the mRNA transcripts, and when a detectable reaction is produced post binding, the transducer captures said reaction and converts it to measurable values, indicating the quantity, presence and the developmental stage of the fungus.

12 Claims, 17 Drawing Sheets

Specification includes a Sequence Listing.

(51) Int. Cl.
    *C12Q 1/28*        (2006.01)
    *G01N 33/00*       (2006.01)
(52) U.S. Cl.
    CPC .. *G01N 33/0098* (2013.01); *B01L 2200/0652* (2013.01); *B01L 2200/16* (2013.01); *B01L 2300/0627* (2013.01)

(56) References Cited

U.S. PATENT DOCUMENTS

| | | | | |
|---|---|---|---|---|
| 2018/0038815 | A1* | 2/2018 | Gu | G01N 27/12 |
| 2018/0246089 | A1 | 8/2018 | Chou et al. | |
| 2019/0144929 | A1 | 5/2019 | Abudayyeh et al. | |

FOREIGN PATENT DOCUMENTS

| | | | |
|---|---|---|---|
| CN | 104164363 | A | 11/2014 |
| DE | 102014105129 | B3 | 7/2015 |
| EP | 2304420 | A2 | 4/2011 |
| WO | 2017025984 | A1 | 2/2017 |
| WO | 2019071142 | A1 | 4/2019 |

OTHER PUBLICATIONS

Leroch, M., Kleber, A., Silva, E., Coenen, T., Koppenhofer, D., Shmaryahu, A., . . . & Hahn, M. (2013) Transcriptome profiling of Botrytis cinerea conidial germination reveals upregulation of infection-related genes during the prepenetration stage. Eukaryotic cell, 12(4), 614-626. (Year: 2013).*

ENDURE (European Network for Durable Exploitation of crop protection strategies) (2007). Deliverable DR4.7, Project No. 031499. Review of factors influencing the success or failure of biocontrol and recommended orientation for new R&D projects. Project start date: Jan. 1, 2007.

Lui et al. (2009). Nucleic Acid-based Detection of Bacterial Pathogens Using Integrated Microfluidic Platform Systems. Sensors (Basel). 2009;9(5):3713-44. doi: 10.3390/s90503713. Epub May 18, 2009. PMID: 22412335; PMCID: PMC3297159.

Ragazzo-Sanchez et al. (2011). Molecular identification of the fungus causing postharvest rot in jackfruit. Mexican Journal of Mycology. 2011;34:9-15. Available online at: https://www.redalyc.org/articulo.oa?id=88321339002.

Rateni et al. (2017). Smartphone-Based Food Diagnostic Technologies: A Review. Sensors (Basel). Jun. 20, 2017;17 (6):1453. doi: 10.3390/s17061453. PMID: 28632188; PMCID: PMC5492046.

Wu et al. (2017). Rapid Waterborne Pathogen Detection with Mobile Electronics. Sensors (Basel). Jun. 9, 2017;17 (6):1348. doi: 10.3390/s17061348. PMID: 28598391; PMCID: PMC5492157.

Farber et al. (2018). Detection and Identification of Plant Pathogens on Maize Kernels with a Hand-Held Raman Spectrometer. Anal. Chem. 2018, 90, 5, 3009-3012. https://doi.org/10.1021/acs.analchem. 8b00222.

Oluwaseun et al. (2018). Biosensors: A Fast-Growing Technology for Pathogen Detection in Agriculture and Food Sector. In Rinken, T., & Kivirand, K. (Eds.). (2018). Biosensing Technologies for the Detection of Pathogens—A Prospective Way for Rapid Analysis. InTech. doi: 10.5772/intechopen.69579.

Udriste et al. (2018). Early detection methods for apple fungal pathogens during postharvest period. Fruit Growing Research. 34. 147-152. 10.33045/fgr.v34.2018.27.

Lastochkina et al. (2019). *Bacillus* Spp.: Efficient Biotic Strategy to Control Postharvest Diseases of Fruits and Vegetables. Plants (Basel). Apr. 12, 2019;8(4):97. doi: 10.3390/plants8040097. PMID: 31013814; PMCID: PMC6524353.

Abdullah et al. (2018). Real-Time PCR for Diagnosing and Quantifying Co-infection by Two Globally Distributed Fungal Pathogens of Wheat. Front Plant Sci. Aug. 9, 2018;9:1086. doi: 10.3389/fpls. 2018.01086. PMID: 30140271; PMCID: PMC6095046.

Ahrberg et al. (2016). Handheld real-time PCR device. Lab Chip. Feb. 7, 2016;16(3):586-92. doi: 10.1039/c5lc01415h. PMID: 26753557; PMCID: PMC4773913.

Moore (2012). Portable device to detect pathogens in 30 minutes. CNET. Retrieved from: https://www.cnet.com/tech/computing/portable-device-to-detect-pathogens-in-30-minutes/.

Aslan (2005). Annealed silver-island films for applications in metal-enhanced fluorescence: interpretation in terms of radiating plasmons. J Fluoresc. Sep. 2005;15(5):643-54. doi: 10.1007/s10895-005-2970-z. PMID: 16341780; PMCID: PMC2793390.

Aslan et al. (2005). Fast and slow deposition of silver nanorods on planar surfaces: application to metal-enhanced fluorescence. J Phys Chem B. Mar. 3, 2005;109(8):3157-62. doi: 10.1021/jp045186t. PMID: 16851335; PMCID: PMC6848857.

Aslan et al. (2005). Metal-enhanced fluorescence: an emerging tool in biotechnology. Curr Opin Biotechnol. Feb. 2005;16(1):55-62. doi: 10.1016/j.copbio.2005.01.001. PMID: 15722016; PMCID: PMC6853068.

De Silva et al. (2016). Mycosphere Essays 9: Defining biotrophs and hemibiotrophs. Mycosphere. 7. 545-559. 10.5943/mycosphere/7/5/2.

Duvall et al (2015). Optical Imaging of Paramagnetic Bead-DNA Aggregation Inhibition Allows for Low Copy Number Detection of Infectious Pathogens. PLoS ONE 10(6): e0129830. doi: 10.1371/journal.pone.0129830.

Eun et al. (2002). Detection of Two Orchid Viruses Using Quartz Crystal Microbalance-Based DNA Biosensors. Phytopathology. Jun. 2002;92(6):654-8. doi: 10.1094/Phyto.2002.92.6.654. PMID: 18944263.

Hermansen, A. et al. (2012). Detection and prediction of post harvest carrot diseases. Eur J Plant Pathol 133, 211-228 (2012). https://doi.org/10.1007/s10658-011-9896-x.

Ahlberg, L. (2013). Cradle turns smart phone into handheld biosensor. Illinois News Bureau, Retrieved from: https://news.illinois.edu/view/6367/204805.

Kohl et al. (2018). Dynamics of post-harvest pathogens *Neofabraea* spp. and *Cadophora* spp. in plant residues in Dutch apple and pear orchards. Plant Pathology. 67. 10.1111/ppa.12854.

Koo et al. (2013). Development of a Real-Time Microchip PCR System for Portable Plant Disease Diagnosis. PLoS ONE 8(12): e82704. doi:10.1371/journal.pone.0082704.

Krezel et al. (2001). Coordination of heavy metals by dithiothreitol, a commonly used thiolgroup protectant. J Inorg Biochem. Mar. 2001;84(1-2):77-88. doi: 10.1016/s0162-0134(00)00212-9. PMID: 11330484.

Lau et al. (2017). Advanced DNA-Based Point-of-Care Diagnostic Methods for Plant Diseases Detection. Front Plant Sci. Dec. 6, 2017;8:2016. doi: 10.3389/fpls.2017.02016. PMID: 29375588; PMCID: PMC5770625.

Martinelli et al. (2015). Advanced methods of plant disease detection. A review. Agronomy for Sustainable Development, 2015, 35 (1), pp. 1-25. 10.1007/s13593-014-0246-1.

Mendes et al. (2009). Development of an electrochemical immunosensor for Phakopsora pachyrhizi detection in the early diagnosis of soybean rust. Article J. Braz. Chem. Soc. 20. 795-801. 10.1590/S0103-50532009000400023.

Mendes et al. (2009). Surface plasmon resonance immunosensor for early diagnosis of Asianrust on soybean leaves. Biosens Bioelectron. Apr. 15, 2009;24(8):2483-7. doi: 10.1016/j.bios.2008.12.033. Epub Dec. 30, 2008. PMID: 19200709.

Morel et al. (2018). Exploring the potential of PROCOSINE and close-range hyperspectral imaging to study the effects of fungal

(56) References Cited

OTHER PUBLICATIONS diseases on leaf physiology. Sci Rep 8, 15933 (2018). https://doi.org/10.1038/s41598-018-34429-0.

Jayanath et al. (2018). Development of a portable electrochemical loop mediated isothermal amplification (LAMP) device for detection of hepatitis B virus. RSC Adv., 2018,8, 34954-34959.

Papadakis et al. (2015). Bacteria Murmur: Application of an Acoustic Biosensor for Plant Pathogen Detection. PLoS ONE 10(7): e0132773. doi:10.1371/journal.pone.0132773.

Hu et al. (2019). Pathogen Detection and Microbiome Analysis of Infected Wheat Using a Portable DNA Sequencer. Phytobiomes Journal. 3. 10.1094/Pbiomes-01-19-0004-R.

Rajapaksha et al. (2019). A review of methods for the detection of pathogenic microorganisms. Analyst, 2019, 144, 396. DOI: 10.1039/c8an01488d.

Skottrup et al. (2008). Towards on-site pathogen detection using antibody-based sensors. Biosens Bioelectron. Nov. 15, 2008;24(3):339-48. doi: 10.1016/j.bios.2008.06.045. Epub Jul. 6, 2008. PMID: 18675543.

Srinivasan et al. (2015). Development and Applications of Portable Biosensors. J Lab Autom. Aug. 2015;20 (4):365-89. doi: 10.1177/2211068215581349. Epub Apr. 15, 2015. PMID: 25878051.

Tomlinson et al. (2005). On-site DNA extraction and real-time PCR for detection of Phytophthora ramorum in the field. Appl Environ Microbiol. Nov. 2005;71(11):6702-10. doi: 10.1128/AEM.71.11.6702-6710.2005. PMID: 16269700; PMCID: PMC1287659.

Vidic et al. (2019). Point-of-Need DNA Testing for Detection of Foodborne Pathogenic Bacteria. Sensors (Basel). Mar. 4, 2019;19(5):1100. doi: 10.3390/s19051100. PMID: 30836707; PMCID: PMC6427207.

Wickes et al. (2018). Molecular diagnostics in medical mycology. Nat Commun 9, 5135 (2018). https://doi.org/10.1038/s41467-018-07556-5.

Huang et al. (2018). An Integrated Real-Time Electrochemical LAMP Device for Pathogenic Bacteria Detection in Food. Electroanalysis. 30. 10.1002/elan.201800382.

Wongkaew et al. (2014). Diagnosis of Sugarcane White Leaf Disease Using the Highly Sensitive DNA Based Voltammetric Electrochemical Determination. American Journal of Plant Sciences. 5. 2256-2268. 10.4236/ajps.2014.515240.

PCT International Preliminary Report on Patentability for International Application No. PCT/IL2020/051272, issued May 17, 2022, 6pp.

European Patent Office, Extended European Search Report for European Patent Application No. 20898502.8, dated Jul. 28, 2023, 13pp.

Maeda Y, Sugiyama Y, Lim TK, Harada M, Yoshino T, Matsunaga T, Tanaka T. Rapid discrimination of fungal species by the colony fingerprinting. Biosens Bioelectron. Dec. 15, 2019; 146:111747. doi: 10.1016/j.bios.2019.111747. Epub Sep. 30, 2019. PMID: 31586763.

Prusky, Dov & Lichter, Amnon. (2008). Mechanisms modulating fungal attack in post-harvest pathogen interactions and their control. European Journal of Plant Pathology. 121. 281-289. 10.1007/s10658-007-9257-y.

Barad S, Sela N, Dubey AK, Kumar D, Luria N, Ment D, Cohen S, Schaffer AA, Prusky D. Differential gene expression in tomato fruit and Colletotrichum gloeosporioides during colonization of the RNAi-SIPH tomato line with reduced fruit acidity and higher pH. BMC Genomics. Aug. 4, 2017;18(1):579. doi: 10.1186/s12864-017-3961-6. PMID: 28778147; PMCID: PMC5545021.

Palou, Lluís & Sánchez-Torres, Paloma & Montesinos-Herrero, Clara & Taberner, Verònica. (2016). Incidence and etiology of postharvest fungal diseases of loquat fruit (*Eriobotrya japonica* (Thunb.) Lindl. cv. 'Algerie') in Alacant province (Spain). European Journal of Plant Pathology. 146. 10.1007/s10658-016-0964-0.

Harpaz D, Alkan N, Eltzov E. The Incorporation of Amplified Metal-Enhanced Fluorescence in a CMOS-Based Biosensor Increased the Detection Sensitivity of a DNA Marker of the Pathogenic Fungus *Colletotrichum gloeosporioides*. Biosensors (Basel). Dec. 13, 2020;10(12):204. doi: 10.3390/bios10120204. PMID: 33322238; PMCID: PMC7764091.

European Patent Office, First Examination Report for European Patent Application No. 20 898 502.8, dated Sep. 12, 2024, 9pp.

Bilkiss, M., Shiddiky, M. J., & Ford, R. (2019). Advanced Diagnostic Approaches for Necrotrophic Fungal Pathogens of Temperate Legumes With a Focus on *Botrytis* spp. Frontiers in microbiology, 10, 1889. Aug. 14, 2019 (Aug. 14, 2019) whole document.

Leroch, M., Kleber, A., Silva, E., Coenen, T., Koppenhofer, D., Shmaryahu, A., . . . & Hahn, M. (2013). Transcriptome profiling of Botrytis cinerea conidial germination reveals upregulation of infection-related genes during the prepenetration stage. Eukaryotic cell, 12(4), 614-626. Feb. 15, 2013 (Feb. 15, 2013) whole document, especially abstract; p. 615, 2nd para; p. 623, 3rd and 4th para; Tables S2-S4.

Fang, Y., & Ramasamy, R. P. (2015). Current and prospective methods for plant disease detection. Biosensors, 5(3), 537-561. Aug. 6, 2015 (Aug. 6, 2015) whole document.

Tang, L., Yu, X., Zhang, L., Zhang, L., Chen, L., Zou, S., . . . & Dong, H. (2020). Mitochondrial FgEch1 is responsible for conidiation and full virulence in Fusarium graminearum. Current genetics, 66(2), 361-371. Aug. 28, 2019 (Aug. 28, 2019) whole document, especially abstact; p. 362, 2nd para; p. 368, 2nd para.

DeAngelis, M. M., Wang, D. G., & Hawkins, T. L. (1995). Solid-phase reversible immobilization for the isolation of PCR products. Nucleic acids research, 23(22), 4 742. Nov. 25, 1995 (Nov. 25, 1995) whole document.

International Search Report for PCT/IL2020/051272 Completed Mar. 11, 2021; Mailed Mar. 11, 2021 4 pages.

Written Opinion for PCT/IL2020/051272 Completed Mar. 11, 2021; Mailed Mar. 11, 2021 5 pages.

Okawa, K., OECD Food, Agriculture and Fisheries Papers, No. 75, OECD Publishing, Paris, 2015).

Dean, R., et al., "The Top 10 fungal pathogens in molecular plant pathology". Molecular Plant Pathology 13, 414-430, 2012.

Rahul, S.N. et al., "Challenges in postharvest management of fungal diseases in fruits and vegetables—a review." South Asian J. Food Technol. Environ 1, 126-130, 2015.

Tripathi, P. and Dubey, N.K., "Exploitation of natural products as an alternative strategy to control postharvest fungal rotting of fruit and vegetables",Postharvest Biology and Technology 32, 235-245, 2004).

Droby, S. and Lichter, A., ""Post-harvest Botrytis infection: etiology, development and management, Botrytis: Biology, pathology and control."" Springer, pp. 349-367, 2007, 2014.

Palou, L., "Chapter 2—*Penicillium digitatum, Penicillium italicum* (Green Mold, Blue Mold), In: Bautista-Banos, S. (Ed.), Postharvest Decay." Academic Press, San Diego, pp. 45-102, 2014.

Prusky, D., Alkan, N., Mengiste, T., Fluhr, "Quiescent and necrotrophic lifestyle choice during postharvest disease development", R., Annual Review of Phytopathology 51, 155-176, 2013).

Alkan, N. et al, "Simultaneous transcriptome analysis of Colletotrichum gloeosporioides and tomato fruit pathosystem reveals novel fungal pathogenicity and fruit defense strategies" New Phytologist 205, 801-815, 2015).

Baker, R.J., "CMOS circuit design, layout, and simulation", The institute of electrical and electronics engineers, 2005.

Zamir, D. et al. "Detection of quiescent fungi in harvested fruit using CMOS biosensor: A proof of concept study", Talanta, 2020).

Zhou, S. et al, "A highly integrated real-time digital PCR device for accurate DNA quantitative analysis", Biosensors and Bioelectronics 128, 151-158, 2019).

* cited by examiner

100

Fig. 4A
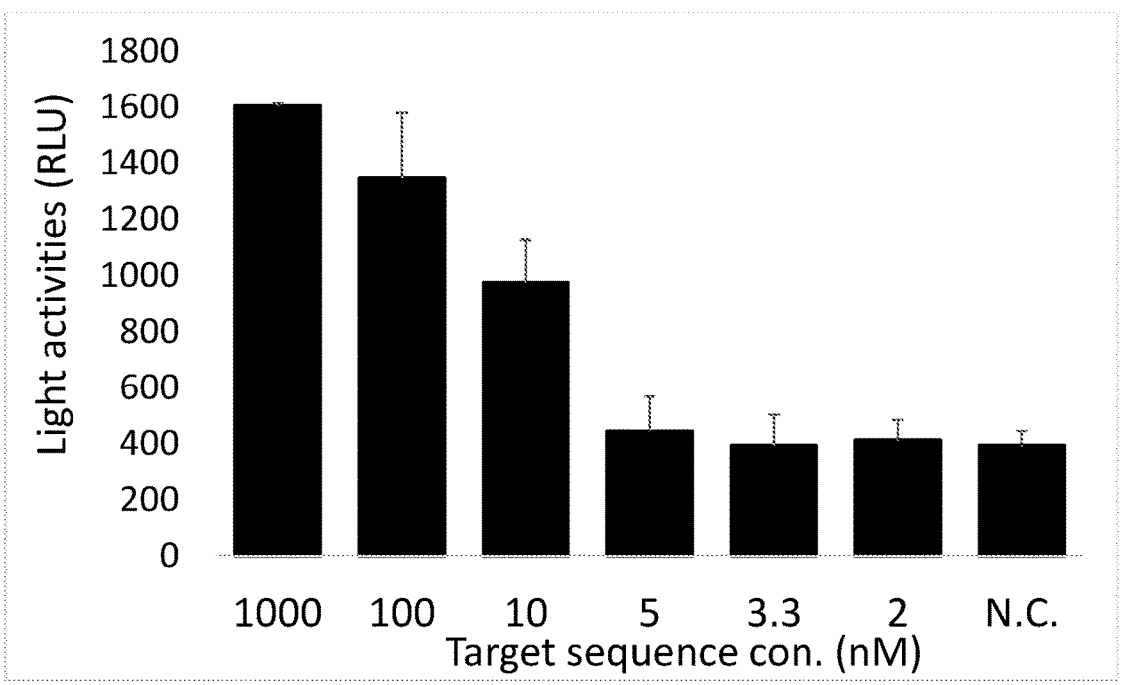
Fig. 4B
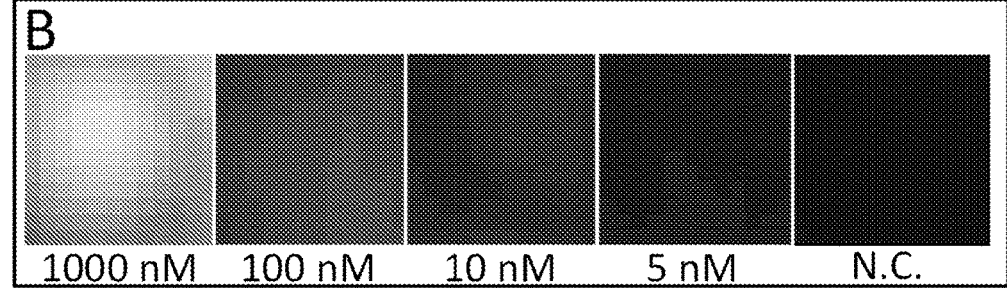
Figure 4

Fig. 13A
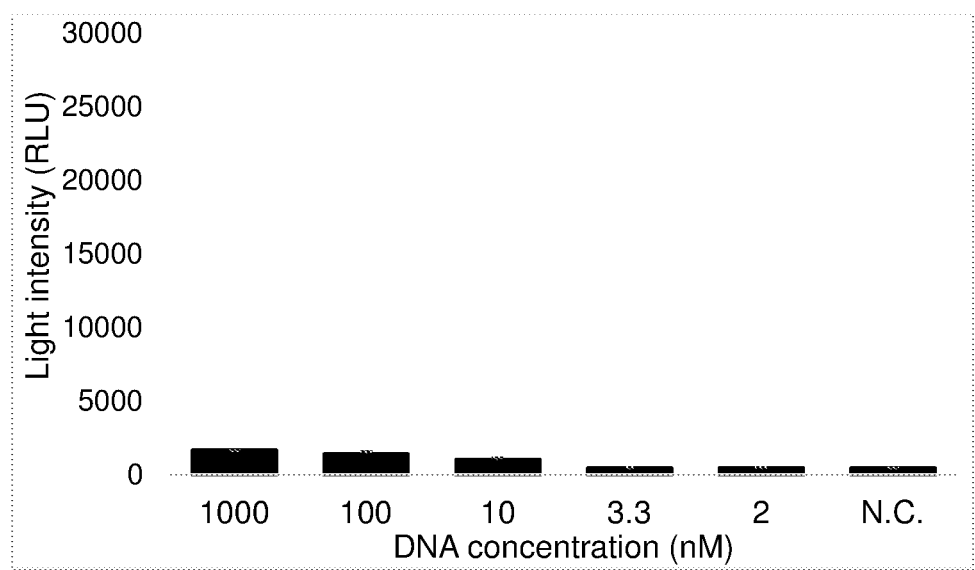
Fig. 13B
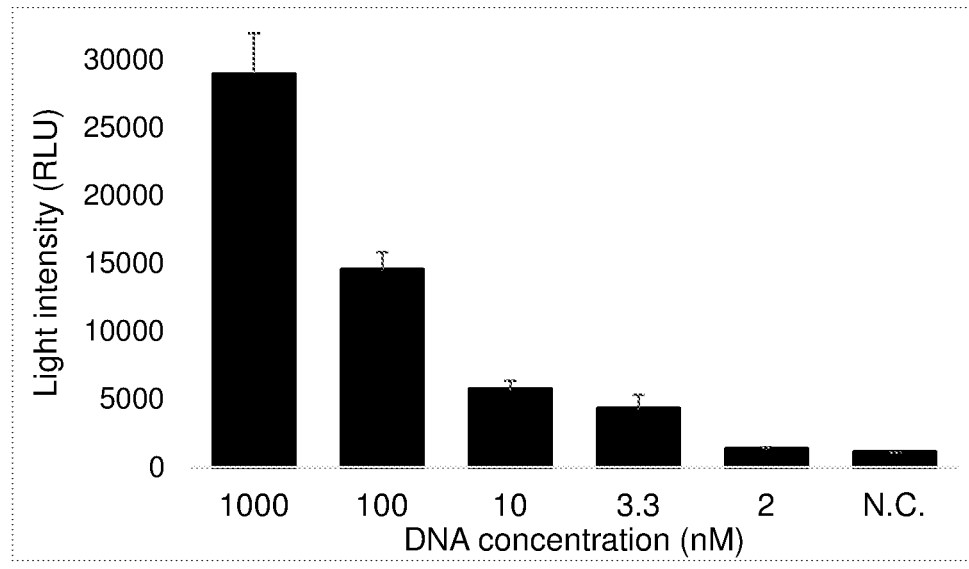
Figure 13

Fig. 14A
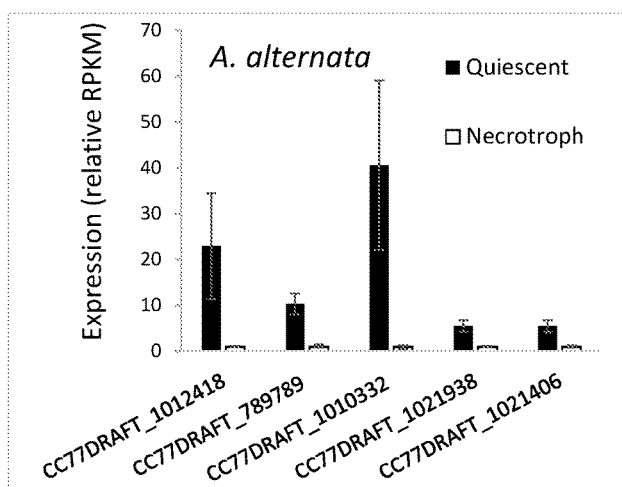
Fig. 14B
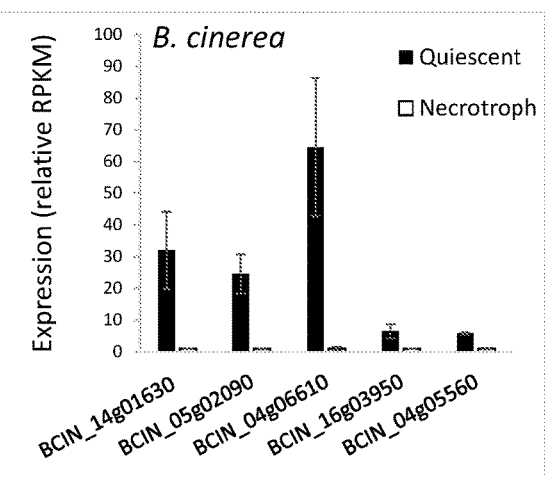
Fig. 14C
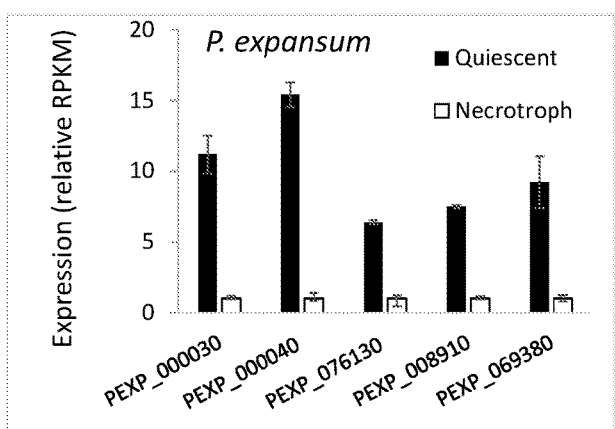
Figure 14

SEQUENCE LISTING

<160> NUMBER OF SEQ ID NOS: 5

<210> SEQ ID NO 1
<211> LENGTH: 18
<212> TYPE: DNA
<213> ORGANISM: Colletotrichum gloeosporioides

<400> SEQUENCE: 1
tgaggcgtgg gaagcaac                                            18

<210> SEQ ID NO 2
<211> LENGTH: 20
<212> TYPE: DNA
<213> ORGANISM: Colletotrichum gloeosporioides

<400> SEQUENCE: 2
atgcaccgta gcgaccagag                                          20

<210> SEQ ID NO 3
<211> LENGTH: 123
<212> TYPE: DNA
<213> ORGANISM: Colletotrichum gloeosporioides

<400> SEQUENCE: 3
cccaagctca taggactgtc taaggcgagc cacgtcacga ccactggaga cgtgtatccc      60
gtcaccgatc cactcgtcaa tgggctgttc tcaaagttgc ttcccacgcc tcaacacaca     120
gtc                                                                    123

<210> SEQ ID NO 4
<211> LENGTH: 123

-continued

```
<212> TYPE: DNA
<213> ORGANISM: Colletotrichum gloeosporioides

<400> SEQUENCE: 4
tcgtcttggg tctctggtcg ctacggtgca tctctcatgc gctcagtctc tgtgagacgc      60
gagtgaactt cgttttactg gttaaagaac ggggaaggaa gacaacgaac cacgactatt     120
tct                                                                    123

<210> SEQ ID NO 5
<211> LENGTH: 123
<212> TYPE: DNA
<213> ORGANISM: Colletotrichum gloeosporioides

<400> SEQUENCE: 5
tggaagtccg gtccatgctc gcgtgtatcc tgatatggga cacggccagg ttttggaggc      60
cgccagggct gatatcgctg cttggatcgc cgcgagattt gaaggagttc ccgttgagaa     120
gac                                                                    123
```

DEVICE AND METHODS FOR DETECTING FUNGAL PATHOGENICITY IN POSTHARVEST PRODUCE

This application is a National Phase of PCT Patent Application No. PCT/IL2020/051272 having International filing date of Dec. 9, 2020, which claims the benefit of priority of U.S. Provisional Patent Application No. 62/945,238, filed Dec. 9, 2019, the contents of which are all incorporated herein by reference in their entirety.

SEQUENCE LISTING

The instant application contains a Sequence Listing which has been submitted electronically in ASCII txt. format and is hereby incorporated by reference in its entirety. Said ASCII copy, is named 08107-P0015A-seq-listing-1371-T-21-PCT-corrected-OCT-2022.txt and is 1,495 bytes in size. Said ASCII copy was created on Oct. 26, 2022.

FIELD OF THE INVENTION

The present invention relates to the field of agriculture, and more particularly the present invention concerns CMOS-based sensor for the detection of fungi in the latent stage of their life cycle in postharvest fruits.

BACKGROUND OF THE INVENTION

The problem of postharvest food losses is a major concern, having been estimated at 40% to 50% of harvested crops worldwide, mostly due to physiological deterioration and rots caused by fungi (see "Market and trade impacts of food loss and waste reduction", Okawa, K., OECD Food, Agriculture and Fisheries Papers, No. 75, OECD Publishing, Paris, 2015). The conventional technologies for detecting postharvest pathogenic fungi (namely PCR and ELISA) are sensitive and precise, but are costly, have complicated protocols and are not portable, making these applications less than optimal for agricultural uses in the fields or greenhouses. Therefore, those applications are not commonly used in packinghouses. Furthermore, while the above-mentioned technologies can indicate the presence of these microorganisms in crops, there is no evaluation of their pathogenicity state. Fungi from several genera may cause postharvest decay of fresh produce (see "The Top 10 fungal pathogens in molecular plant pathology". Dean, R., et al., Molecular Plant Pathology 13, 414-430, 2012; "Challenges in postharvest management of fungal diseases in fruits and vegetables—a review." Rahul, S. N. et al., South Asian J. Food Technol. Environ 1, 126-130, 2015 and "Exploitation of natural products as an alternative strategy to control postharvest fungal rotting of fruit and vegetables", Tripathi, P. and Dubey, N. K., Postharvest Biology and Technology 32, 235-245, 2004). Usually, after penetrating the immature fruit, the fungi remain quiescent, and only switch to their pathogenic state after storage and ripening, initiating the active attack. The quiescent infections are microscopic and cannot be visually detected during packaging or subsequent transport (see "Post-harvest *Botrytis* infection: etiology, development and management, *Botrytis*: Biology, pathology and control." Droby, S. and Lichter, A., Springer, pp. 349-367, 2007, 2014. "Chapter 2—*Penicillium digitatum, Penicillium italicum* (Green Mold, Blue Mold), In: Bautista-Banos, S. (Ed.), Postharvest Decay." Palou, L., Academic Press, San Diego, pp. 45-102, 2014 and "Quiescent and necrotrophic lifestyle choice during postharvest disease development", Prusky, D., Alkan, N., Mengiste, T., Fluhr, R., Annual Review of Phytopathology 51, 155-176, 2013).

With over 470 widely distributed host genera (mango, avocado and strawberry, to name a few), *Colletotrichum gloeosporioides* is one of the most common disease agents in postharvest fruits. After conidial germination, *C. gloeosporioides* usually undergoes three different developmental stages: appressoria (penetration), quiescence (latent stage), and the necrotrophic stage, which causes decay. In the first stage, *C. gloeosporioides* penetrates the fruit cuticle, and it then remains in an extended quiescent state until fruit ripening. At fruit ripening, the fungal pathogen switches to the necrotrophic stage, resulting in anthracnose disease in the fruit. During these different stages, the fungal pathogen significantly upregulates stage-specific transcripts (see "Simultaneous transcriptome analysis of *Colletotrichum gloeosporioides* and tomato fruit pathosystem reveals novel fungal pathogenicity and fruit defense strategies", Alkan, N. et al, New Phytologist 205, 801-815, 2015).

Using biosensors for RNA detection may be the easiest, cheapest and fastest method to recognize the presence of pathogens in crops. Typical biosensors are built from three parts: bioreporter, transducer and interface, the latter immobilizing the first part on the second. Mass balance, optical and quartz crystal microbalance are the most common measurement approaches for DNA detection. Recent advances in the optical field have led to the development of sensitive, low-cost and small-size photodetectors based on complementary metal oxide semiconductor (CMOS) technology (see "CMOS circuit design, layout, and simulation", Baker, R. J., the institute of electrical and electronics engineers, 2005., and "Detection of quiescent fungi in harvested fruit using CMOS biosensor: A proof of concept study", Zamir, D. et al. Talanta, 2020). CMOS-based biosensors have been used for bacterial detection in environmental air and water samples for toxicity evaluation tests, and as PCR-process monitoring tools (see "A highly integrated real-time digital PCR device for accurate DNA quantitative analysis", Zhou, S. et al, Biosensors and Bioelectronics 128, 151-158, 2019).

EP patent document 2304420A4 to Jonathan M. Rothberg discloses methods and apparatuses relating to large scale FET arrays for analyte detection and measurement of inter alia, nucleic acids of pathogens.

US patent document 8213017 to Max Wiki discloses an analytical system and method for generating and metering optical signals. The system can comprise a CMOS arrays and is utilized for determining chemical, biochemical or biological analytes, including nucleic acids of pathogens.

CA patent document 2460212C to Don Straus discloses methods for rapidly and sensitively identifying cellular and viral targets in medical, industrial, and environmental samples. This method includes binding nucleic acids of bacteria, viruses and fungi.

Thus, there is an unmet need for portable, sensitive, inexpensive and simple applications for agricultural uses, which will not only detect the presence of the microorganisms in the crops before causing decay, but also evaluate their presence during their quiescent stage in postharvest fruits, before extensive damages are done.

BRIEF DESCRIPTION OF THE FIGURES

The accompanying drawings, which are included to provide a further understanding of the invention and are incorporated in and constitute a part of this specification, illustrate embodiments of the invention and together with the description serve to explain the principles of the invention.

FIG. 4 depicting a graphical presentation of the system's responsiveness to different concentrations of a specific DNA sequence;

FIG. 13 depicting the effect of the optimization steps on the sensitivity of the system of the present invention to *Colletotrichum gloeosporioides* fungi;

FIG. 14 depicting the relative expression of fungal transcripts of *Alternaria alternata, Botrytis cinerea,* and *Penicillium expansum* colonizing tomato fruit at their quiescent and necrotrophic stage;

SUMMARY OF THE INVENTION

Figure 1:
FIG. 1 depicting a schematic presentation of the system of the present invention and the measuring procedure.
Figure 1:
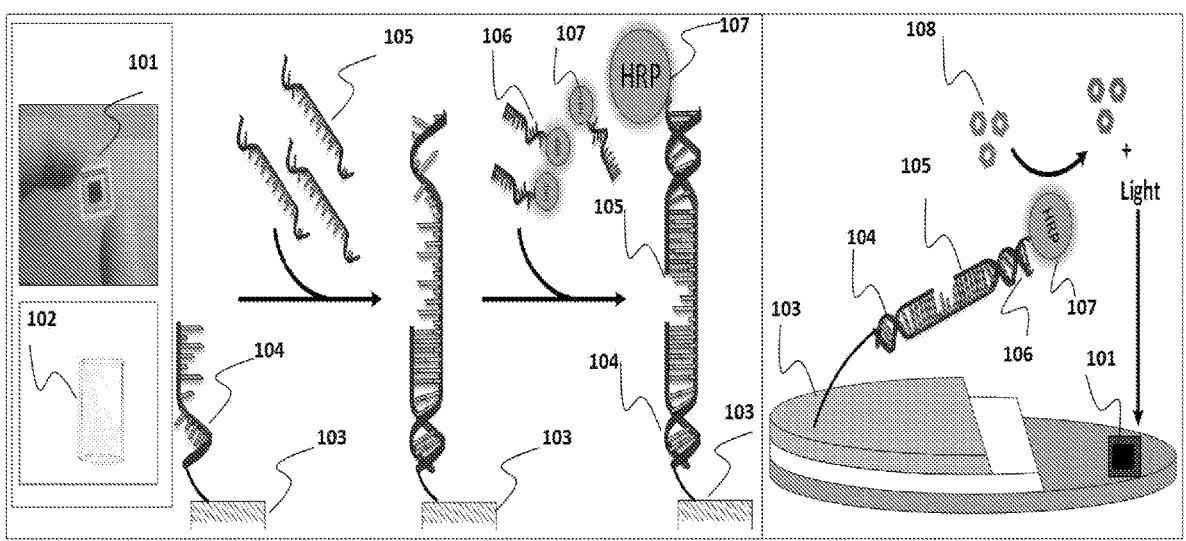

It is thus one object of the present invention to disclose a system for detecting fungi in a plant tissue, the system comprises:

a. a measuring transducer;

b. a surface; and c. nucleic acid strands immobilized onto the surface;

wherein the system comes in contact with a mixture comprising:

(i) target RNA sequences form the fungi; and (ii) reporter strands conjugated to a signal-generating component;

further wherein the target RNA sequences from the fungi anneal to the immobilized nucleic acid strands, the reporter strands bind to the target RNA sequence, the signal-generating component is configured to generate a detectable reaction, further wherein the system is configured to indicate the developmental stage of the fungi.

It is another object of the present invention to disclose the system as described above, wherein the fungi are selected from a group consisting of: *Magnaporthe oryzae, Botrytis cinerea, Colletotrichum gloeosporioides, Puccinia* spp, *Fusarium graminearum, Fusarium oxysporum, Blumeria graminis, Mycosphaerella graminicola, Colletotrichum* spp, *Ustilago maydis, Diplodia natalensis, Alternaria alternata, Penicillium digitatum, Penicillium expansum, Pestalotia psidii, Monilinia fructicola, Monilinia laxa, Neonectria ditissima, Rhizopus stolonifer* and *Melampsora lini*.

It is another object of the present invention to disclose the system as described above, wherein the fungi are selected from a group consisting of: *Botrytis cinerea, Alternaria alternata, Colletotrichum gloeosporioides* and *Penicillium expansum*.

It is another object of the present invention to disclose the system as described above, wherein the plant tissue is a postharvest produce.

It is another object of the present invention to disclose the system as described above, wherein the measuring transducer is selected from a group consisting of: optical means, electrochemical means, acoustic means, thermal means, mass-balance means and any combination thereof.

It is another object of the present invention to disclose the system as described above, wherein the optical means are selected from a group consisting of CMOS, CCD, PMT, plate readers, cameras and any combination thereof.

It is another object of the present invention to disclose the system as described above, wherein the electrochemical means are selected from a group consisting of: electrodes, electrode cells, screen-printed electrodes with conductimetric, amperometric, impedimetric or potentiometric components and any combination thereof.

It is another object of the present invention to disclose the system as described above, wherein the surface is selected from a group consisting of: silica, metal, glass, plastic, organic polymers, non-organic polymers, thiolated particles, nanomaterials, modified silica and any combination thereof.

It is another object of the present invention to disclose the system as described above, wherein the nucleic acid strands immobilized onto the surface are fixed to the surface by immobilization techniques selected from a group consisting of: adsorption, covalent bonding, entrapment, cross-linking, self-assembling, encapsulation and any combination thereof.

It is another object of the present invention to disclose the system as described above, wherein the nucleic acid strands immobilized onto the surface and the reporter strands are selected from a group consisting of: deoxyribonucleic acid, ribonucleic acid, hybridized strand comprising deoxyribonucleic acid and ribonucleic acid and any combination thereof.

It is another object of the present invention to disclose the system as described above, wherein the signal-generating component is selected from a group consisting of: enzymes, fluorescence-based molecules, luminescence-based molecules, piezoelectric biosensors, thermometric biosensors, optical biosensors, affinity binding molecules, colorimetric materials and any combination thereof.

It is another object of the present invention to disclose the system as described above, wherein the enzyme is horseradish peroxidase.

It is another object of the present invention to disclose the system as described above, wherein the target RNA sequences are characteristic of different developmental stages in the life cycle of the fungi.

It is another object of the present invention to disclose the system as described above, wherein the developmental stages are selected from a group consisting of: appressoria, quiescence and the necrotrophic stage.

It is another object of the present invention to disclose the system as described above, wherein the target RNA sequence is enoyl-CoA-hydratase/isomerase.

It is another object of the present invention to disclose the system as described above, wherein the target RNA sequence is SEQ ID NO 3.

It is another object of the present invention to disclose the system as described above, wherein the reporter strand is SEQ ID NO 1, conjugated to horseradish peroxidase at the 5' end.

It is another object of the present invention to disclose the system as described above, wherein the nucleic acid strand immobilized onto the surface is SEQ ID NO 2, comprising fluorescein isothiocyanate at the 5' end and a thiol group at the 3' end.

It is another object of the present invention to disclose the system as described above, wherein the system is configured to detect the target RNA from the fungi at a concentration of about 3.3 nM.

It is another object of the present invention to disclose the system as described above, wherein the system is portable.

It is another object of the present invention to disclose a method for detecting fungi and evaluating fungal inoculum rate in a plant tissue, comprising steps of:

a. obtaining the system of claim 1;
    b. obtaining an RNA sample from the plant tissue;
    c. loading the RNA sample and reporter strands onto the system of claim 1;
    d. washing the system of claim 1;
    e. performing a reaction to detect a signal;
    f. measuring the signal; and
    g. linking the signal to the presence or quantity of the fungi and to the developmental stage in which the fungi are.

It is another object of the present invention to disclose the method as described above, wherein the plant tissue is a postharvest produce.

It is another object of the present invention to disclose the method as described above, wherein the reaction to detect the signal is selected from a group consisting of: fluorescence-based reaction, luminescence-based reaction, enzyme-substrate reactions, antigen-antibody reactions, affinity-based reactions and any combination thereof.

It is another object of the present invention to disclose the method as described above, wherein the reaction to detect the signal is the oxidation of a substrate by horseradish peroxidase.

It is another object of the present invention to disclose the method as described above, wherein the substrate is selected from a group consisting of: luminol, AmplexRed (10-Acetyl-3,7-dihydroxyphenoxazine), homovanillic acid, TMB (3,3',5,5'-Tetramethylbenzidine), OPD (o-Phenylenediamine), AEC (3-Amino-9-ethylcarbazole), ABTS (2,2'-azino-bis(3-ethylbenzothiazoline-6-sulfonic acid)), and DAB (3,3'-Diaminobenzidine).

It is another object of the present invention to disclose the method as described above, wherein the developmental stage of the fungi is selected from a group consisting of: appressoria, quiescence and the necrotrophic stage.

It is another object of the present invention to disclose the method as described above, wherein the fungi are selected from a group consisting of: *Magnaporthe oryzae, Botrytis cinerea, Colletotrichum gloeosporioides, Puccinia* spp, *Fusarium graminearum, Fusarium oxysporum, Blumeria graminis, Mycosphaerella graminicola, Colletotrichum* spp,

*Ustilago maydis, Diplodia natalensis, Alternaria alternata, Penicillium digitatum, Penicillium expansum, Pestalotia psidii, Monilinia fructicola, Monilinia laxa, Neonectria ditissima, Rhizopus stolonifer* and *Melampsora lini.*

It is another object of the present invention to disclose the method as described above, wherein the fungi are selected from a group consisting of: *Botrytis cinerea, Alternaria alternata, Colletotrichum gloeosporioides* and *Penicillium expansum.*

It is another object of the present invention to disclose the method as described above, wherein the measuring is executed by quantitative or qualitative means.

It is another object of the present invention to disclose the method as described above, wherein the reporter strand is SEQ ID NO 1, conjugated to horseradish peroxidase at the 5' end.

It is another object of the present invention to disclose the method as described above, wherein the evaluation of fungal inoculum and the developmental stage in the life cycle of the fungi are configured to be combined with data mining tools and bioinformatic tools.

DETAILED DESCRIPTION OF THE PREFERRED EMBODIMENTS

The following description is provided, alongside all chapters of the present invention, so as to enable any person skilled in the art to make use of the invention and sets forth the best modes contemplated by the inventor of carrying out this invention. Various modifications, however, are adapted to remain apparent to those skilled in the art, since the generic principles of the present invention have been defined specifically to provide a device based on measuring transducer and nucleic acid annealing, and methods for detecting fungi at different developmental stages in harvested products. The present invention discloses a system comprising a CMOS-based sensor coupled with specific mRNA sequences that are upregulated in fungi, such as *C. gloeosporioides* during its quiescent stage. The identification process is based on the sandwich approach, where strands complementary to the fungal mRNA sequences are immobilized on the CMOS surface. With the presence of the target analyte (which can be for example, in a non-limiting way, samples from postharvest products), these complementary strands specifically anneal to the mRNA transcripts found in the sample. The quantity of the fungal quiescent mRNA sequences is evaluated using a reporter strand that is further added to the system and anneals to the quiescent mRNA transcript. This creates a surface complex that includes mRNA and reporter strands, which remains on the CMOS surface after numerous washing steps. Signal generation is then assessed by conventional methods, for example a luminescent enzymatic reaction of horseradish peroxidase (HRP) enzyme conjugated to the reporter strand. This technology not only allows pathogen detection in fresh agricultural produce, but also identifies the unseen quiescent fungi inside the fruit, before it further develops and necrotizes the produce.

Furthermore, the present disclosure describes optimization and calibration steps rendering the system of the present invention more sensitive and accurate, thus capable of detecting low concentrations of fungal nucleic acids (starting from about 3.3 nM).

As used herein after, the term "about" refers to any value being up to 25% lower or greater the defined measure.

As used herein after, the term "developmental stage" refers to any distinct stage in the fungus life cycle. This could be for example, appressoria, quiescence or the necrotrophic stage.

As used herein after, the term "appressoria" or "appressorium" refers to a specialized cellular structure, typically found in various pathogenic fungi early on in development, which infect plant. The appressorium is an organ, forming from germinating conidia, and is dedicated to allow the penetration to the host's surface using turgor pressure.

As used herein after, the term "quiescence" refers to a stage in the fungus life cycle. After penetrating a plant host, the fungus can remain latent (or dormant) inside the plant tissues for weeks or months, which is hard to detect or monitor without sophisticated equipment. The fungus can remain inactive inside the plant tissues, or develop slowly (depending on the ripening stage of the fruit). Usually after storage and ripening, if the conditions become in favor of the fungal infection, the fungus switches to the necrotrophic stage and starts growing rapidly, forming lesions and decay in the host's tissues. As any distinct stage in the fungus life cycle, unique mRNA transcripts are upregulated during the quiescence stage, thus, characterizing it transcriptionally.

As used herein after, the term "necrotrophic stage" refers to the stage in the fungus life cycle, which follows the quiescence stage. During this stage, the fungal infection becomes highly active, progressing inside the plant tissues and eventually causing decay and necrotic lesions.

As used herein after, the term "measuring transducer" refers to any component capable of capturing a signal and converting it to measurable values. A measuring transducer can be for example an optical transducer, an electrochemical transducer, acoustic detectors, thermal detectors, mass-balance means and any other transducers known in the art.

As used herein after, the term "optical transducer" refers to any photodetector or camera which is capable of reading or capturing light signals generated by the system of the present invention, and converting it to numerical values, representing the concentrations of the fungal mRNA transcripts found in the tested plant sample. The optical photodetector can be selected in a non-binding fashion from the following options: CMOS (complementary metal-oxide-semiconductor), CCD (charge-coupled device), PMT (photomultiplier tubes), or any other cameras, commercial plate readers or plate readers known in the art.

As used herein after, the term "CMOS" or "Complementary metal-oxide-semiconductor" refers to a fabrication technology based on metal-oxide-semiconductor field-effect transistor. CMOS technology is used among other things for generating integrated circuit chips, such as microprocessors, microcontrollers, and memory chips, and is also used for analog circuits such as image sensors (CMOS sensors). The latter consists of pixel sensor unit cells, where each cell has a photodetector and one or more active transistors. This technology is capable of capturing light signals and converting them into measurable numerical values. In the present disclosure, the system comprises a CMOS-based sensor and nucleic acid strands coupled with a signal-generating component, such as the horseradish peroxidase (HRP). HRP is an enzyme which can generate a chemiluminescent reaction, whose resultant signals are then detected and evaluated by the CMOS sensor.

As used herein after, the term "signal-generating system/component" refers to any system, whose components react in such a fashion that a detectable signal (such as light or heat) is produced, and can be further converted to numerical, measurable values. This system may consist of enzymes (such as horseradish peroxidase), fluorescence-based molecules (fluorophores), luminescence-based molecules, optical biosensors, piezoelectric biosensors, thermometric biosensors, colorimetric materials (compounds which change their colors based on the chemical reaction), affinity binding molecules and any other form of systems known in the art.

As used herein after, the term "immobilized strand" or "surface strand" refers to any nucleic acid sequence (DNA, RNA, or hybrid DNA-RNA strand), which is bound to the surface of the system of the present invention, and anneals to specific fungal mRNA sequences found in the tested sample.

As used herein after, the term "target strand" refers to any RNA sequence extracted from a tested sample ("analyte", which could be for example, a fruit which is suspected of being contaminated with a fungal infection). The target strand is loaded onto the system of the present invention, and anneals to the immobilized strand on one end and to the reporter strand on the other end.

As used herein after, the term "reporter strand" refers to any nucleic acid sequence (DNA, RNA, or hybrid DNA-RNA strand), which is conjugated to any component of a signal-generating system on one side, and can also anneal to the mRNA transcripts (target strands) of the tested sample, which is bound to the immobilized strand.

As used herein after, the term "surface" refers to the base of the system of the present invention. This part binds the immobilized strands, which anneal to specific mRNA sequences (target strands) of the tested sample (analyte). The surface is further connected to a measuring transducer (such as the CMOS sensor). Various materials having the ability to bind nucleic acids might be integrated in this part, including, but not limited to, silver particles, gold particles, coper particles, zinc particles, thiolated particles, silica, plastics, biotin-streptavidin, additional organic or inorganic materials or components that efficiently bind nucleic acids, such as magnetic beads, polymers, nanomaterials etc. The immobilization of the immobilized strands to the surface of the system of the present invention can be carried out via numerous approaches known in the art, such as adsorption, covalent bonding, entrapment, cross-linking, self-assembling, encapsulation etc.

In a preferred embodiment of the present invention, the system is designed to detect the quiescent stage of fungi in postharvest produce, when the fungal infection is still at low concentrations and invisible to the naked eye.

In another preferred embodiment of the present invention, the system is portable, and the detection of the fungal infection is carried out in the field or in a greenhouse.

In yet another preferred embodiment of the present invention, the system comprises a surface, to which is immobilized a nucleic acid strand ("immobilized strand"), which specifically anneals to mRNA transcripts form a tested sample (a fruit which may be contaminated with a fungal infection, for instance). Then, a reporter strand is added to the system, capable of annealing to the mRNA transcripts, and is also conjugated to a signal-generating system or molecules (such as HRP). Subsequently, the appropriate substrates which activate the signal-generating system are added (for example, luminol for HRP), and the generated luminescence reaction is captured by the CMOS sensor and translated into numerical, measurable values, indicating the concentrations of the fungal RNA in the fruit. As the immobilized strands are segments of genes upregulated in a specific developmental stage of the fungus, the system of the present invention can accurately indicate the developmental stage of the fungus colonizing the tested plant tissue.

In yet another preferred embodiment of the present invention, the system is configured to calculate the concentrations of the fungal RNA in the postharvest produce, and also to indicate the developmental stage at which the fungus is in its life cycle (appressorium, quiescence or necrotrophic).

In yet another preferred embodiment of the present invention, the strands (immobilized, target and reporter strands) are transcripts (or segments thereof) of genes specifically upregulated in the quiescent stage of the fungus.

In yet another preferred embodiment of the present invention, the surface of the system is configured to bind nucleic acid strands ("immobilized strands") by conventional means, such as adsorption, covalent bonding, entrapment, cross-linking, self-assembling, encapsulation and more. The surface of the system can comprise metals, nanoparticles, inorganic or organic polymers to ensure proper binding of the immobilized strands.

In yet another preferred embodiment of the present invention, the surface of the system is coupled with a measuring transducer. This measuring transducer can be any optical or electrochemical detector/sensor known in the art, for example: CMOS, CCD, PMT, any other cameras, commercial plate readers or plate readers known in the art, electrodes, electrode cells, and screen-printed electrodes using conductimetric, amperometric, impedimetric or potentiometric approaches.

In yet another preferred embodiment of the present invention, the system can be further optimized and calibrated, making it capable of detecting concentrations of fungal mRNA transcripts at concentrations of about 3 nM.

In yet another preferred embodiment of the present invention, the system can be combined with publicly available data-mining and bioinformatic tools, thus, rendering the system a predictive tool for assessing shelf-life of postharvest produce.

Example 1

One of the main challenges in DNA-based sensor development is immobilization of the receptor molecules (immobilized strands) to the solid-phase (the surface) with the transducer. The bioreporter molecules at the top of the sensor not only need to retain their activity after the immobilization step, but they also have to be sensitive and specific to the target analyte. In this section, an example of the different components of the system of the present invention is disclosed. DNA strands immobilized on the glass surface had to bind the complementary target RNA strands of the tested sample, and then complete the hybridization process with the reporter strand on their opposite end. Reference is now made to FIG. 1. schematically illustrating the system of the present invention (100) and the measuring procedure. The proposed system is based on a measuring transducer, such as a CMOS photodetector (101) and a glass tube (102) with silver nanoparticles on the surface (103), modified with immobilized DNA strands (104). A complementary RNA sequence (105) in the tested sample (the target strand) anneals specifically to the surface-immobilized DNA strand (104) on one end and to the complementary reporter strand (106) linked to horseradish peroxidase (107) on the other end. Following the addition of the proper substrate (108), the horseradish peroxidase (107) linked to the reporter strand (106) produces light. This light is detected by the CMOS photodetector (101) and represented as measurable light values, indicating the concentration of fungal RNA in the tested sample. Based on the sequences of the immobilized strands (104), the system of the present invention (100) is also capable of indicating the developmental stage of the fungi (appressoria, quiescence or necrotrophic stage).

Example 2

As noted above, some of the components comprising the system of the present invention can vary. For instance, the surface of the system can comprise various materials which bind the immobilized strands. The following description discloses the activation procedures of the system of the present invention, in a specific non-binding example, wherein the surface is made of glass (modified silica) and silver nanoparticles, the reporter strand is conjugated to HRP, and the measuring transducer is an optical photodetector, CMOS:

Surface Activation:

To form the sensor surface, 350-µL flat-bottom glass tubes (CSI, #I025-630) were incubated in MeOH:HCl solution (1:1, v/v) at room temperature for 20 min. Then, the tubes were dipped in double distilled water (DDW) and sonicated in a sonication bath (JK-OCD30A, MRC, Holon, Israel) for 20 min. The tubes were exposed to piranha solution (H2O2: H2SO4, 3:7, v/v) at 90° C. for 60 min. Then they were rinsed with DDW, dried with $N_2$ and exposed to 3-glycidoxypropyltrimethoxysilane at 60° C. for 60 min. Finally, the tubes were rinsed with double-distilled water, dried and subjected to silver-deposition procedures.

Silver Deposition:

Silver liquid deposition was performed as follows: 500 µL fresh 5% (w/v) NaOH solution was added to a silver nitrate solution (0.22 g in 26 mL of DDW) with rapid stirring. After the formation of a dark-brownish precipitate, a little under 1 mL of ammonium hydroxide was added to the deposition solution until the precipitate dissolved. The clear solution was cooled to 5° C. by placing the beaker in an ice bath. Tubes were placed in the silver deposition solution, fresh D-glucose solution (0.35 g in 4 mL of water) was added, and the mixture was stirred for 2 min. Then, the solution was warmed to 30° C. Tubes were incubated in the deposition solution until a silver layer formed on the glass surface, then washed with water and dried.

Fungal Inoculation and Sample Preparation:

Single-spore cultures of *Colletotrichum gloeosporioides* (isolate Cg-14) obtained from decayed avocado fruit, *Botrytis cinerea* B05.10 and *Penicillium expansum* Pe-21 obtained from decayed apples, and *Alternaria alternata* obtained from persimmon fruits were cultured on $M_3S$. All of the above fungi have a very broad spectrum of hosts, one of the hosts being a tomato fruit. Freshly harvested mature green and red tomato fruit (*Solanum lycopersicum* L.) were used for inoculation with *C. gloeosporioides*, the mature green tomato was inoculated with 7 µL of a conidial suspension ($5\times10^5$ conidia mL$^{-1}$), at 50 inoculation spots per fruit, with six different fruit per biological replicate and 10 biological replicates per treatment. RNA for the appressorium and quiescent stages was collected 19 and 100 hours post-inoculation of the mature green tomato fruit, respectively. For *B. cinerea, P. expansum*, and *A. alternata* the mature green tomato was wound-inoculated by punching with a needle to 1-mm depth and inoculating with 7 µL of a conidial suspension ($5\times10^5$ conidia mL-1). For necrotrophic-stage growth, red fruits were punched with a needle to 1-mm depth and inoculated with 7 µL of a conidial suspension ($5\times10^5$ conidia mL-1) of either of the fungi. Six inoculation spots on each of six different fruits were inoculated per biological replicate, with 10 biological replicates per treatment. RNA for necrotrophic-stage evaluation was collected 48 hours post-inoculation by removing tissue to 0.5 mm depth. All of the collected tissues were stored at −80° C. until use.

DNA Immobilization:

DNA was immobilized on the glass surface by exposing the silver-modified tubes to 20 μL of 1 μM surface-DNA solution diluted with Tris-EDTA buffer for 1 hour at room temperature in the dark. Then, the tubes were washed with Tris-EDTA buffer and exposed to 20 μL of target and reporter strands. Conventional PCR was performed using a Veriti 96-Well Thermal Cycler (Applied Biosystems) with one thermal program cycle (60 seconds at 90° C., then 30 seconds at 75° C., 30 seconds at 65° C. and finally 30 seconds at 53° C.). DNA quality and quantity were measured in the ND-1000 spectrophotometer. Following exposure, tubes were washed with Tris-EDTA buffer and placed on the CMOS sensor or in an in-vivo imaging system (IVIS-100, Perkin Elmer, Waltham, MA, USA) for further light monitoring.

Instrument Setup:

To monitor enzymatic activity, a field-operable biosensor was designed. The sensor [CMOS sensor-ULS solution kit by Anitoa (Palo Alto, CA)] was placed in a light-tight box to prevent light interference. To receive and analyze the data, a specific software developed by Anitoa was used to monitor the luminescent signal and to handle the data in real time. A special holder preventing tube movement during the measuring procedure was combined with the sensor.

CMOS Measurement Procedure:

Light activation from the enzymatic reaction was observed by deposition of 20 μL substrate solution (Luminol:$H_2O_2$, 1:1, v/v) on the CMOS sensor surface and placing tubes above it.

Example 3

Figure 2:
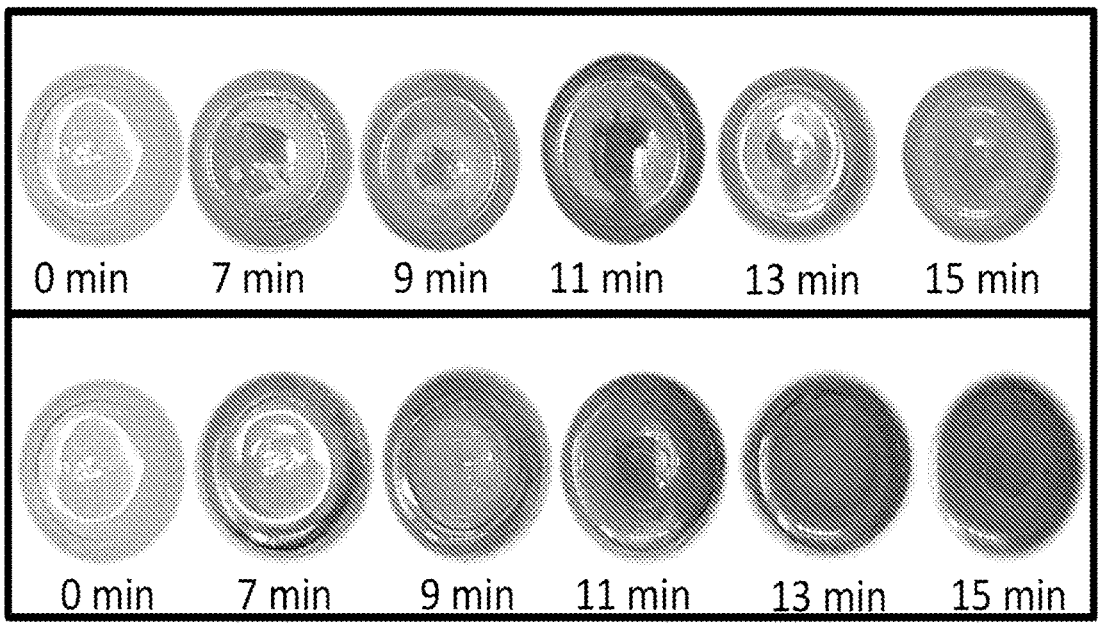
FIG. 2 depicting a presentation of the effect of the silver-deposition reaction with time on silver immobilization on the internal and external surfaces of the system of the present invention.

Reference is now made to FIG. 2. visually depicting the effect of the silver-deposition reaction with time on silver immobilization on the internal (upper panel) and external (lower panel) surfaces of the tube. The first step of the immobilization process is to bind DNA to the silver-modified glass surface. Two different deposition locations on the tube were chosen (i.e., inside and outside surface). First, the effect of reaction time on deposition efficiency was tested. The silver-modification process is a kinetic reaction in which layer formation depends on the exposure time of the glass surface to the deposition solution (see "Metal-enhanced fluorescence: an emerging tool in biotechnology", Aslan et al., Current Opinion in Biotechnology, 16, 55-62, 2005; and "Fast and Slow Deposition of Silver Nanorods on Planar Surfaces: Application to Metal-Enhanced Fluorescence", Aslan et al., The Journal of Physical Chemistry B, 109, 3157-3162, 2005). However, no visible correlations were observed between deposition time and silver uniformity on the inner surface (FIG. 2, upper panel). This might have been due to the difficulty of controlling all surface activation and modification conditions (i.e., washing and drying steps, exposure temperatures and times) during the glass-activation and silver-deposition processes in the small inner tube volume. The tube structure makes it difficult to proceed with the washing and drying steps, which are critical for effective treatment. Therefore, residual water and chemicals may interfere with further silver deposition. Another possible reason for the nonuniform deposition is the inability to control reaction temperatures inside the tube. The inventors therefore proceeded to test external surface modification. The external tube surface, in this case, is much more convenient for efficient drying and washing, and the solution temperature can be easily controlled for optimal modification procedures. Indeed, in this case, and similar to previous studies (see "Annealed Silver-Island Films for Applications in Metal-Enhanced Fluorescence: Interpretation in Terms of Radiating Plasmons", Aslan et al., Journal of Fluorescence 15, 643, 2005), increasing the exposure time induced silver deposition and created more uniform layers (FIG. 2, lower panel). Thus, the external surface-modification procedure was chosen for further experiments.

Example 4

Reference is now made to the effect of DTT on tube-surface stability and DNA immobilization efficiency. Tubes were modified with a silver layer and incubated with thiolated DNA without or with DTT. To optimize the process, different parameters in the deposition protocol were evaluated, such as the effects of deposition temperature, stirring intensity during the immobilization process, and chemical concentrations. In addition, the effect of DTT, a small-molecule redox reagent used as a reducing or "de-protecting" agent for thiolated DNA, on surface-immobilization efficiency was tested. DTT is usually added to thiolated DNA to lower or prevent coupling self-reactions between the terminal sulfur atoms, and it is used in chemistry, biochemistry, peptide-protein reactions and clinical medicine applications. In this study, addition of DTT to the DNA incubation solution not only changed the silver's morphology (e.g., color and opacity) but also had a negative effect on the DNA-immobilization efficiency. In contrast to the glass surface treated only with DNA, there were no visible responses from tubes exposed to the DNA-DTT solution. This might be due to an interaction between the silver surfaces and DTT, which is a strong reducing agent, with a redox potential of −0.33 V at pH 7 (see "Coordination of heavy metals by dithiothreitol, a commonly used thiol group protectant", Krefel et al., Journal of Inorganic Biochemistry 84, 77-88, 2001). It is known that DTT, as well as other SH-containing compounds, strongly bind to silver atoms. Thus, the observed inhibitory effect might be explained by DTT binding to the silver nanoparticles, thereby preventing further DNA immobilization. Changes in the silver color of the samples with DTT supported this assumption. Thus, all further immobilization procedures were performed without adding DTT to the incubation solution.

Example 5

Specificity of the CMOS-based system was assessed using mRNA sequences isolated from *C. gloeosporioides* that were upregulated during the quiescent stage. In order to obtain the RNA sequences, RNA was extracted from 50 mg (fresh weight) of Cg-14 mycelium that was grown for 10 days on $M_3S$ plates, or 100 mg of inoculated tomato fruit tissue from the three different stages (appressorium, quiescent, necrotrophic stage). All of the samples were ground in liquid nitrogen to a fine powder using a mortar and pestle. RNA was extracted from Cg-14 mycelium using the Norgen Biotek Plant/Fungi Total RNA Purification Kit (Thorold, Canada) according to the manufacturer's protocols with 50 mg of the ground mycelium per isolate as starting material. For RNA extraction from inoculated tomato fruit, total RNA was isolated from 100 mg inoculated tomato fruit at each of the three stages using the Spectrum™ Plant Total RNA Kit (Sigma Aldrich, STRN250-1KT) following the manufacturer's protocol.

Figure 3:
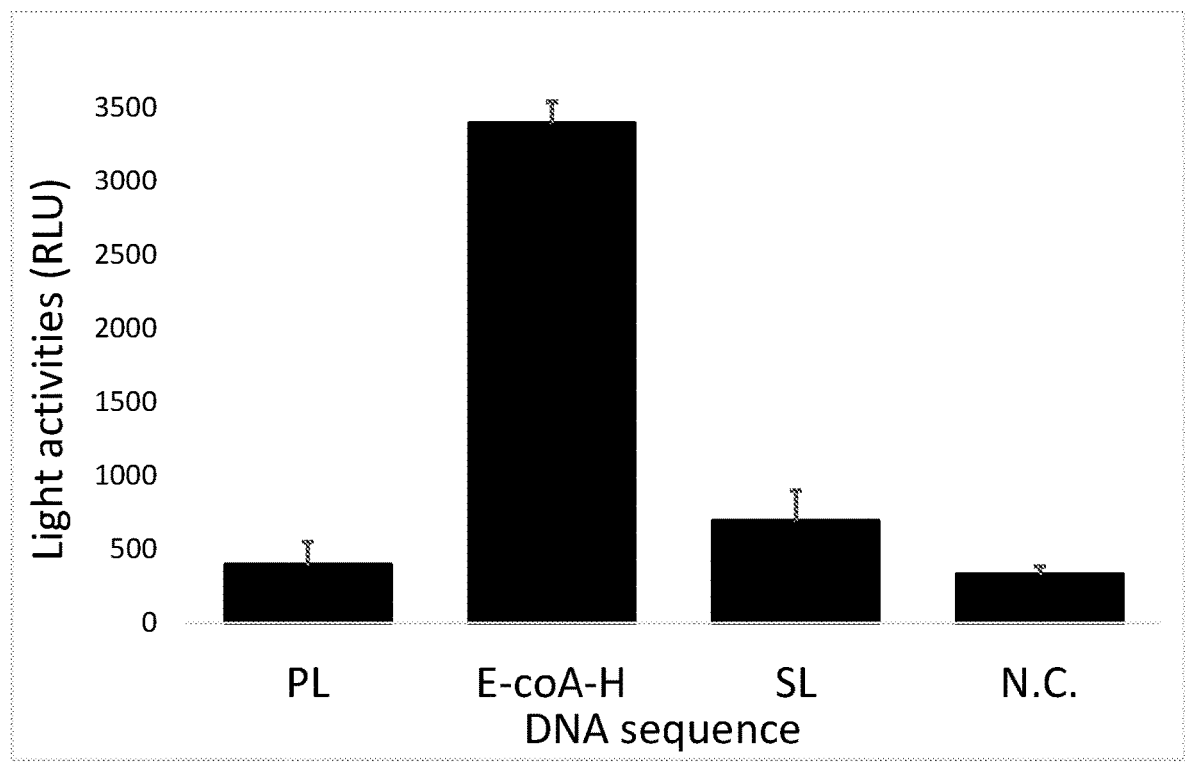
FIG. 3 depicting a graphical presentation of the system's specificity to nucleic acids sequences.

For each experiment, the system of the present invention was operated with three different strands, i.e., surface (immobilized strand), target (from the tested sample), and reporter strand conjugated to HRP. This measuring technology is based on specific nucleic acid hybridization of the immobilized DNA probe on the system. The rationale is that the signal will only be generated in the presence of the target analyte in the sample, which will anneal to the surface DNA strand from one end and to the reporter strands in its opposite direction. The sensor's ability to distinguish between C. gloeosporioides mRNA that is upregulated during the quiescent stage and other tested strands was confirmed by specificity trials. Reference is now made to FIG. 3. demonstrating the specificity of the present invention to (A) a nonspecific DNA sequence (Cgl_00010698; the non-complementary DNA strand of pectate lyase {PL}), (B) a quiescence specific DNA sequence (Cgl_00014454; the complementary strand of enoyl-CoA-hydratase/isomerase {E-coA-H}) and (C) a nonspecific DNA sequence (Cgl_00010395; the noncomplementary DNA strand of secretory lipase {SL}). A negative control (N.C.) shows the response of the system of the present invention to a DNA-free sample. The results graphically depicted in FIG. 3. show that a much higher signal was detected in response to the complementary DNA sequence of the quiescent stage-up-regulated transcript (Cgl_00014454) compared to transcript of other stages, enabling a precise distinction between the specific and nonspecific sensor responses.

(P<0.005 by ANOVA. RLU=relative light units).

Example 6

The sensitivity of the present invention was evaluated by exposing the modified tubes (the surface of the system) to the mixtures with a fixed concentration (100 nM) of the quiescent-stage reporter and surface strands and different concentrations of the target RNA strand. Reference is now made to FIG. 4A graphically depicting the response of the system to different concentrations of specific sequence Cgl_00014454 (enoyl-CoA-hydratase/isomerase), and FIG. 4B depicting the visualization of the light activity on the surface of the tubes exposed to different concentrations of Cgl_00014454 (1000 nM, 100 nM, 10 nM, 5 nM and negative control [NC]).

FIG. 4 demonstrates the system's ability to distinguish between different concentrations of the target RNA strand molecules in solution above a 5 nM threshold of the target sequence. Conventional PCR technology enables a more sensitive DNA detection, but the CMOS application provided similar or higher sensitivity to many other optical-based (see "Chemiluminescent DNA optical fibre sensor for Brettanomyces bruxellensis detection", Cecchini et al., Journal of Biotechnology 157, 25-30, 2012; and "Surface plasmon resonance immunosensor for early diagnosis of Asian rust on soybean leaves", Mendes et al., Biosensors and Bioelectronics 24, 2483-2487, 2009), electrochemical-based (see "Development of an electrochemical immunosensor for Phakopsora pachyrhizi detection in the early diagnosis of soybean rust", Mendes et al., Journal of the Brazilian Chemical Society 20, 795-801, 2009; and "Diagnosis of sugarcane white leaf disease using the highly sensitive DNA based voltammetric electrochemical determination", Wong-kaew, P., and Poosittisak, S., American Journal of Plant Sciences 5, 2256, 2014) and mass-balance-based (see "Detection of two orchid viruses using quartz crystal microbalance-based DNA biosensors", Eun et al., Phytopathology 92, 654-658, 2002; and "Bacteria Murmur: Application of an Acoustic Biosensor for Plant Pathogen Detection", Papadakis et al., PLOS ONE 10, e0132773, 2015) biosensors for pathogen detection in plants.

An additional advantage of the CMOS-based application of the present invention is the active-pixel sensor technology, where each picture element (pixel) has a photodetector and an active amplifier. This not only increases the sensor's sensitivity, but also provides better visualization of the light activity on the surface of the tubes during the measurement process. This effect can be seen in FIG. 4B, with brighter zones above the tube surface and their quantification in FIG. 4A. Furthermore, at all higher tested concentrations (up to 10 nM), the tube dimensions were easily visualized by similar light activities above the tube surface.

(*P<0.005 by ANOVA. RLU, relative light units N.C., negative control).

Example 7

Figure 5:
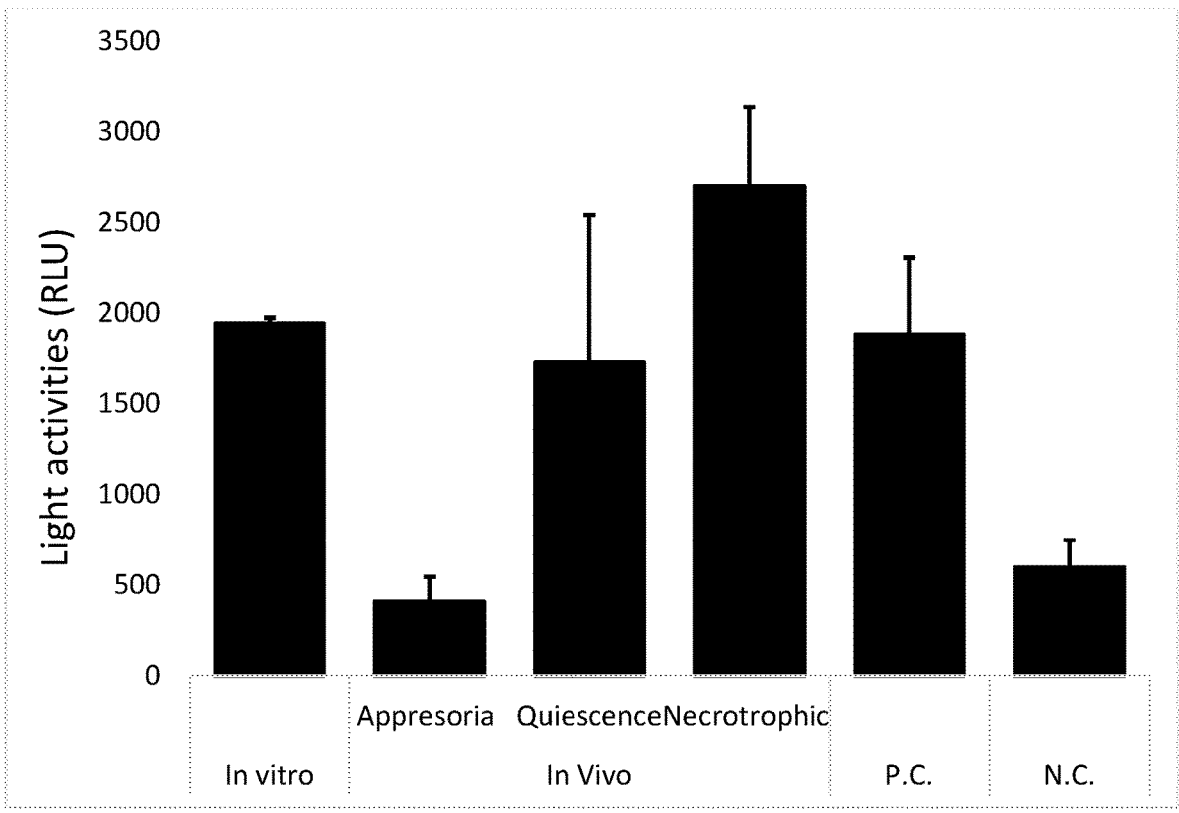
FIG. 5 depicting a graphical presentation of the system's responsiveness to total peel RNA at different *C. gloeosporioides*-infection stages.

Reference is now made to FIG. 5. graphically presenting the response of the present system to total tomato peel RNA at different C. gloeosporioides-infection stages. In parallel, the system of the present invention was exposed to RNA solution extract from fungus grown on the plate (in vitro) and to DNA-free sample extraction (RLU=relative light units; P.C.=positive control; N.C.=negative control, *P<0.005 by ANOVA).

To develop a CMOS-based sensor that will detect quiescent-stage fungi in fruit, the total RNA of the tomato peel was evaluated at different C. gloeosporioides-infection stages. The CMOS biosensor was exposed to RNA extracted from tomato fruits inoculated with C. gloeosporioides at different developmental stages. Postharvest fungal pathogens usually penetrate the fruit before harvest. The fungi then enter a long quiescent and microscopic phase in the immature fruit; when the fruit ripens, the fungi switch to their necrotrophic stage and cause decay. For this CMOS biosensor proof of concept, the focus was on detecting the fungus during its microscopic quiescent stage and looking for mRNA that is highly expressed during fungal quiescence. Application with strands complementary (surface and reporter strands) to these mRNAs, which are induced during quiescence, allows simple and sensitive visualization of this gene expression. FIG. 5 demonstrates the responses of the system to the fungus in vitro (i.e., hyphal growth stage) and at three different in-vivo stages on tomato fruit-appressorium (penetration stage), quiescence (latent stage) and necrotrophic (pathogenic stage). In parallel, the system of the present invention was exposed to the synthesized DNA sequence (as a positive control) and samples without target DNA (as a negative control). Quiescent and necrotrophic stages induced sensor responses compared to the appressorium stage. Thus, the gene enoyl-CoA-hydratase/isomerase is highly induced during the quiescent stage, when the fungi are dormant and their metabolic and transcriptomic activities are significantly reduced (see "Simultaneous transcriptome analysis of Colletotrichum gloeosporioides and tomato fruit pathosystem reveals novel fungal pathogenicity and fruit defense strategies", Alkan, N., New Phytologist 205, 801-815, 2015). Interestingly, the signal was also visible during necrotrophic and pathogenic colonization, when the fungi are highly active and proliferating. As previously discussed in example 6 and FIG. 4, there is a correlation between light intensity and DNA concentration in the sample. Thus, during quiescence, mRNA transcription is induced, with more RNA hybridization to the immobilized surface and reporter sequences, and therefore stronger light emission is observed.

During active pathogenicity, the fungi will grow and proliferate, leading to similar light emission. These results show that the present system is not only able to determine the presence of the pathogens in fresh postharvest produce, but also senses fungi during their microscopic quiescent stage when their metabolism is reduced, and they are not visible to the naked eye.

Example 8

The system of the present invention can be further optimized and calibrated by taking several additional steps, ensuring its enhanced sensitivity, accuracy and specificity. These steps are further described in the following sections and accompanying drawings.

Figure 6:
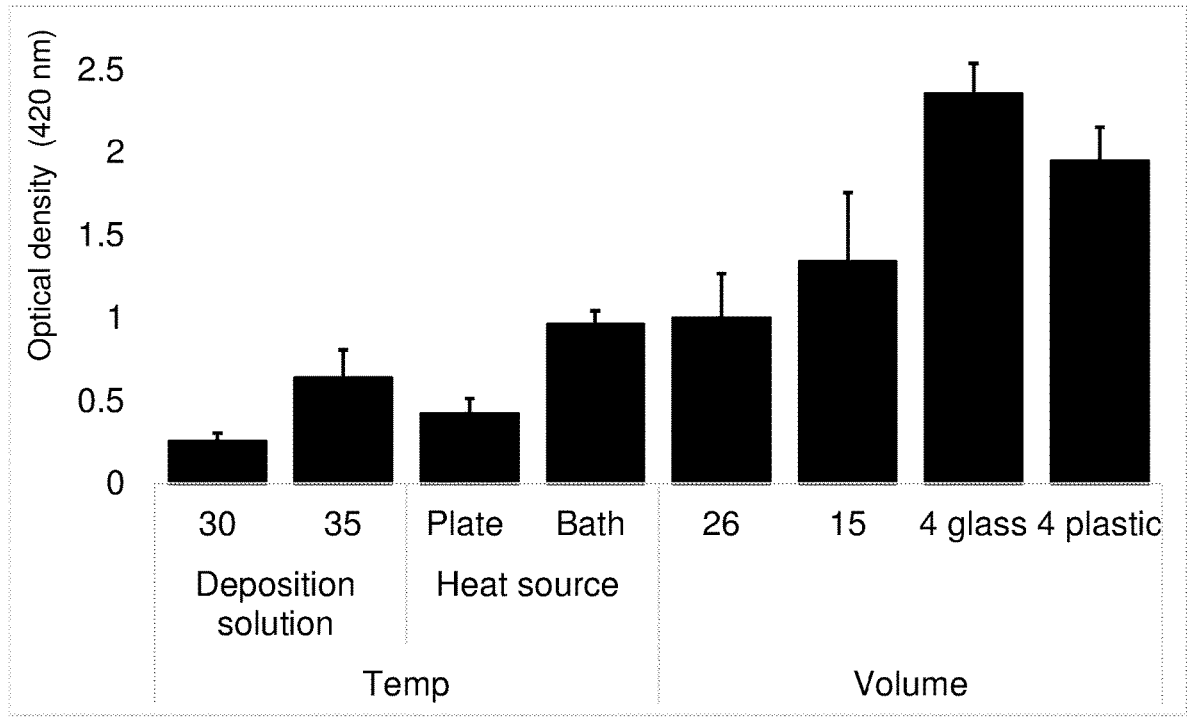
FIG. 6 depicting the effect of different deposition conditions on the efficiency of the silver layer formation.

The effects of different parameters on the efficiency of the silver layer formation were examined, including silver solution temperature and volume, heating mode, and tank material (FIG. 6). The optical density (OD) at 420 nm was compared as an indication of the silver layer formation. Higher optical density values are equivalent to increased amounts of silver that is deposited on the glass surface. From the results, generally, the silver deposition procedure was more efficient in the cases of lower deposition solution volumes and by heating the deposition solution with a water bath as the heating source to a higher temperature. Two silver solution temperatures were tested, and a temperature of 35° C. ($OD_{420\ nm}$=0.638) showed an increased optical density as compared to a temperature of 30° C. ($OD_{420\ nm}$=0.254), indicating 2.5-times increased deposition of silver. Among the two tested heat sources, a 2.3-times increased amount of silver was deposited in the case of a water bath ($OD_{420\ nm}$=0.961) as a heating source as compared to the plate heater ($OD_{420\ nm}$=0.423). Moreover, three different silver deposition solution volumes were examined of 4, 15, and 26 mL. Among the tested solution volumes, 4 mL (glass: $OD_{420\ nm}$=2.354 and plastic: $OD_{420\ nm}$=1.945) showed a 1.76-times and 2.35-times increased deposition of silver, as compared to 15 mL ($OD_{420\ nm}$=1.340) and 26 mL ($OD_{420\ nm}$=1.000), respectively. A possible explanation may be centered around the solution temperature because the silver deposition procedure is highly dependent on the solution temperature. Higher silver deposition solution volumes require a longer heating time; therefore, in a constant deposition time of 9 minutes, higher solution volumes may result in less deposition of silver. In addition, in the case of a 4 mL silver deposition solution, more silver was deposited when the tank material was glass ($OD_{420\ nm}$=2.354), as compared to plastic ($OD_{420\ nm}$=1.945). A possible reason may be the difference in the thermal conductivity coefficients (TCC) between the glass (1.82 (Btu/(hr ft ° F.)) and the polypropylene plastic (0.69 (Btu/(hr ft ° F.))). The higher TCC of glass may result in faster heating of the silver deposition solution, and therefore, may also result in a more efficient silver deposition process. To conclude, the deposition of silver was more efficient with a lower deposition solution volume of 4 mL in a glass tank, and by heating the deposition solution with a water bath to a temperature of 35° C.

Figure 7:
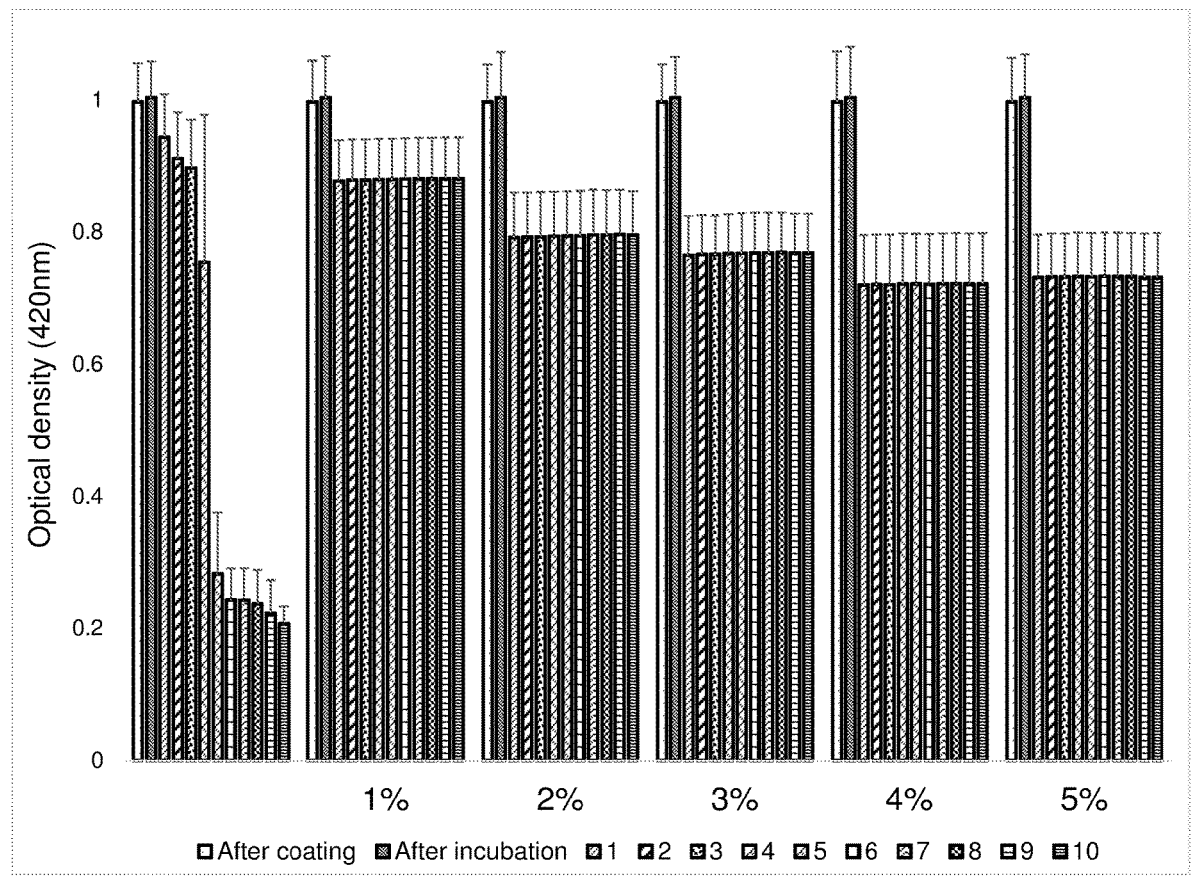
FIG. 7 depicting the effect of blocking treatments with skim milk on the silver layer stability.
Figure 8:
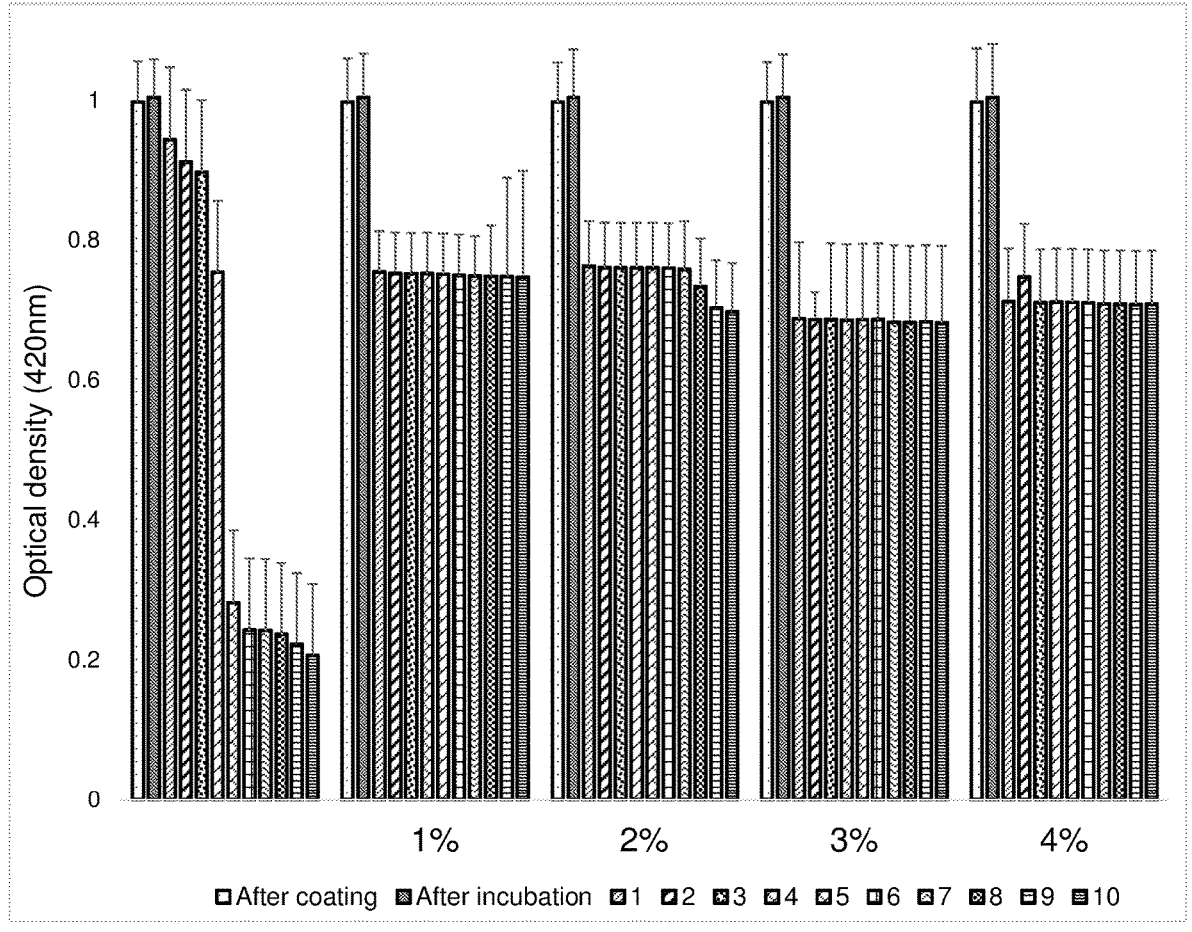
FIG. 8 depicting the effect of blocking treatments with bovine serum albumin (BSA) on the silver layer stability.

To summarize, FIG. 6 shows that for all tested conditions, deposition processes occurring in glass tanks with the lowest deposition solution volumes, heated with the water bath to the highest reaction temperatures (35° C.) demonstrated more efficient silver deposition rates. This may be observed from the higher optical density values, which indicate a greater amount of deposited silver on the glass surface FIG. 7 and FIG. 8 demonstrate the effect of the blocking process on the silver layer stability. To determine the significance of this factor, modified surfaces were treated with different concentrations of skim milk (1%, 2%, 3% 4% and 5% (w/v)) [FIG. 7] and BSA (1%, 2% 3% and 4% (w/v)) [FIG. 8]. Then, the tubes were washed ten times, while the glass surface's optical density was measured after each washing step. For all used blocking agents and at all tested concentrations, an increase of the silver stability during washing steps was observed. Compared to the untreated surfaces (0%), optical density in the blocked tubes decreased only after the first step and then remained constant during all further treatments. An increase in the silver surfaces' stability may be explained by the absorption of the blocker molecules above them (on the glass, silver, and edges). The addition of the blocking layer may prevent nonspecific absorption processes and stabilize the silver layer by creating additional connection forces between fixed metal and glass surface. The creation of such a layer may be observed by decreasing the optical density values after the blocking step.

Figure 9:
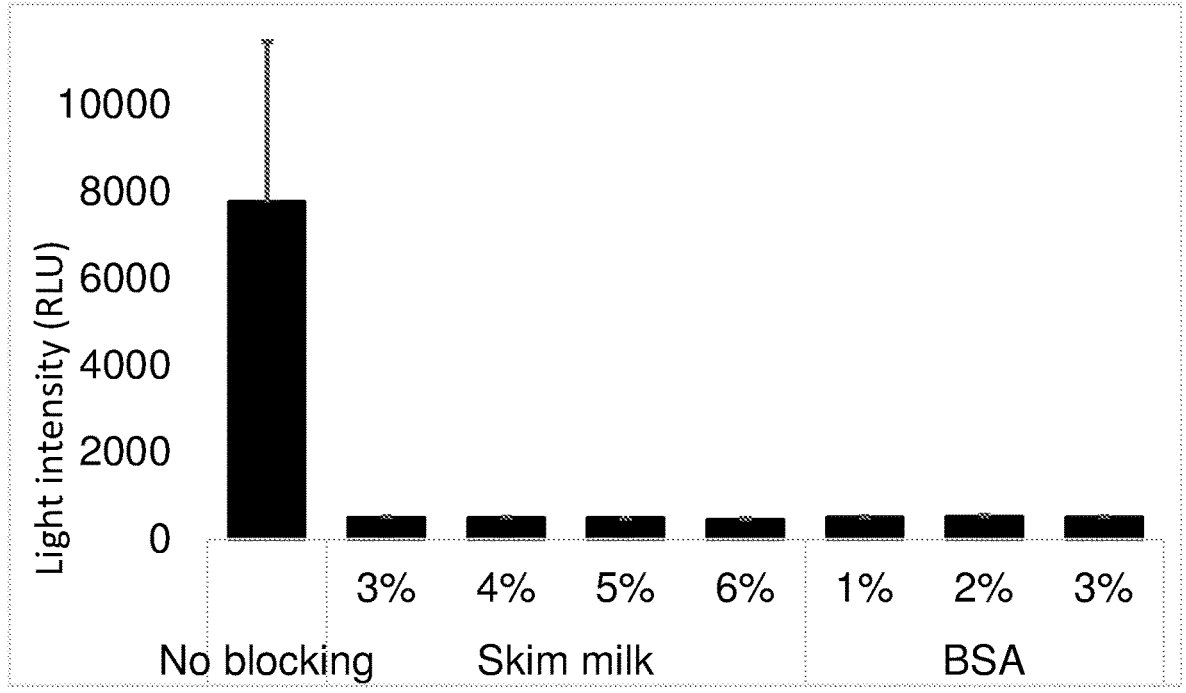
FIG. 9 depicting effect of the blocking step on the DNA nonspecific absorption on the surface of the present system.

FIG. 9 graphically depicts the effect of the blocking step on DNA nonspecific absorption on the glass surface. The graph presents how the non-specificity of the immobilization step was evaluated by blocking silver modified glass surfaces with the different blocking agents (skim milk and BSA) and the light activity was compared to the unblocked tubes. After the blocking step, all tubes were incubated with 100 nM of the DNA-HRP solution (reporter strands), washed and measured by addition HRP substrate ($H_2O_2$+ luminol).

Figure 10:
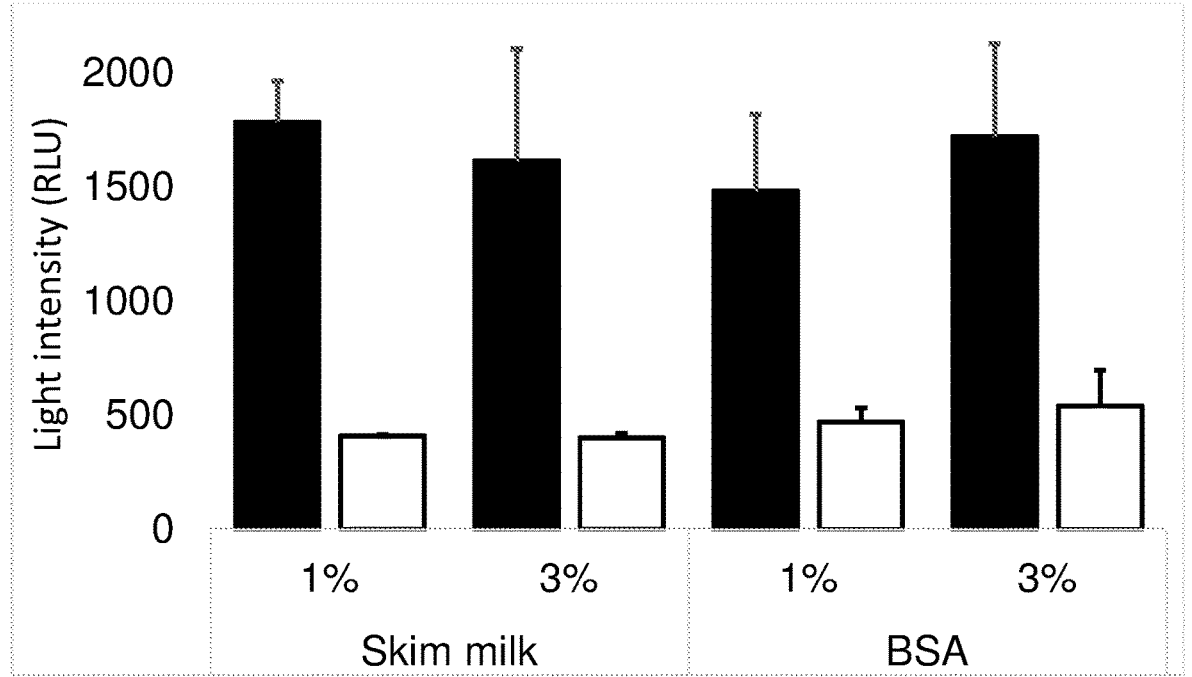
FIG. 10 depicting the effect of the blocking step on the annealing processes specificity of the present system.

FIG. 10 depicts the effect of the blocking step on the annealing processes. Surface DNA modified tubes were blocked with the different blocking agents (skim milk and BSA) and exposed to the reporter strands (DNA strands conjugated to HRP) with and without target analyte (black bars and white bars, respectively). After annealing processes, tubes were washed and measured by addition HRP substrate ($H_2O_2$+luminol).

The objective of this step is to determine an optimal blocking agent to improve DNA hybridization efficiency and prevent non-specific DNA absorption on the silver surface of the present system. Since it is challenging to predict the best blocking agent rationally, a screening experiment was carried out. Two types of blocking agents (skim milk and BSA) at different concentrations were tested. Silver surface with immobilized DNA was incubated with different blocking solutions, washed, and exposed to the reporter strand. Nonspecific DNA absorption processes may be observed from higher light activities of the unblocked than the blocked surfaces. For all tested blockers, unblocked tubes generate 100-fold higher light activity compared to the blocked samples. Such unspecific absorption may produce false-positive responses during further measurements and therefore, blocking steps is essential for correct sensor functionality. Then, the effect of the blockers on mRNA annealing processes was evaluated. Surface DNA modified tubes were blocked with the different blocking agents and concentrations and exposed to the reporter (DNA-HRP) strand with and without target analyte. The blocking step decreases reporter DNA unspecific absorption to the glass surface of the present invention, while any effect on annealing processes was observed. For all tested parameters, similar response patterns were observed. Such uniformity indicates that at tested concentrations, a similar blocking layer is forming for both BSA and skim milk. At the same time, all unused agents are washed out and therefore cannot disturb further annealing processes.

Figure 11:
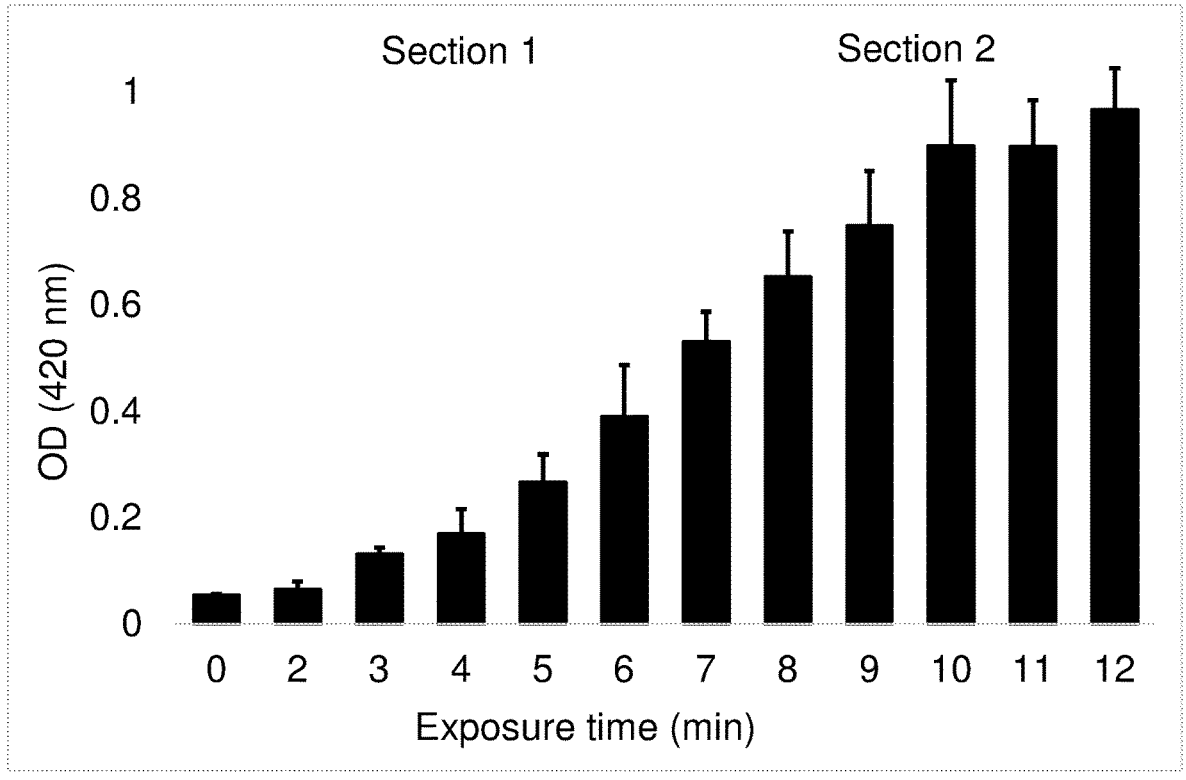
FIG. 11 depicting the effect of the deposition reaction duration on the silver layer formation of the present system.
Figure 12:
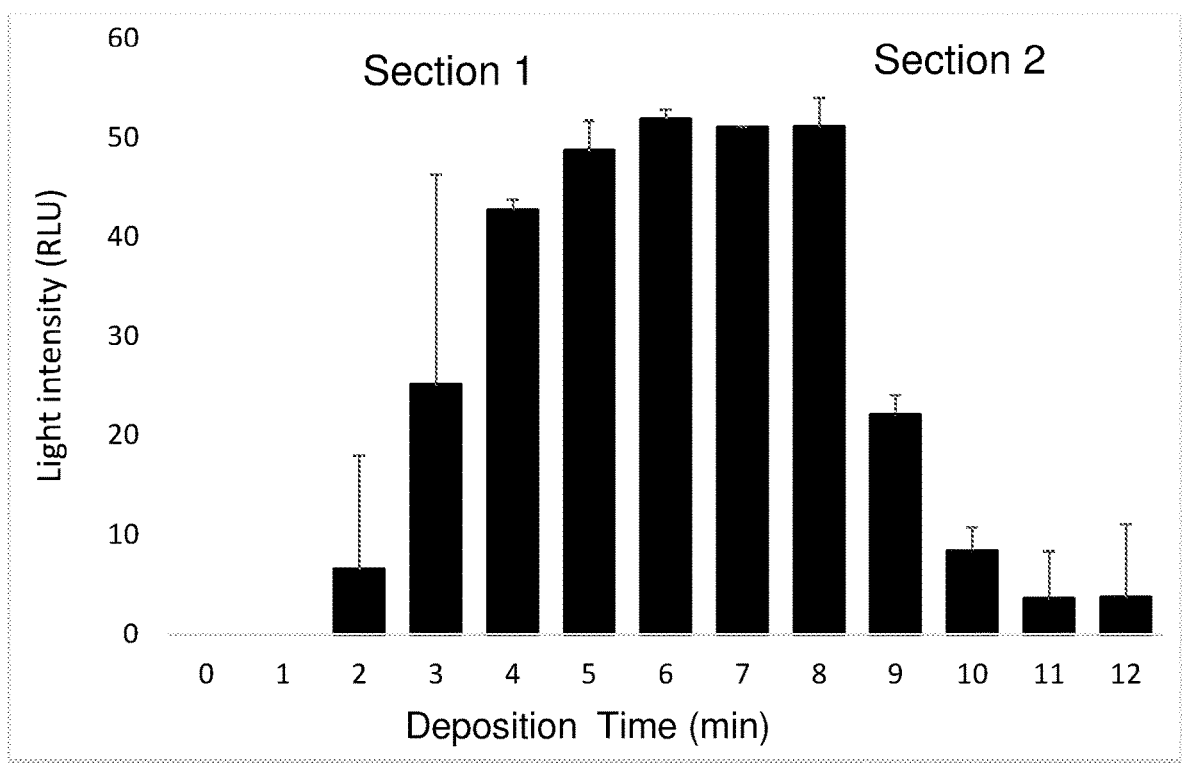
FIG. 12 depicting the effect of the deposition reaction duration on the metal-enhanced fluorescence (MEF) amplification.

Reference is now made to FIG. 11 and FIG. 12 depicting the effect of the silver deposition reaction time on DNA immobilization efficiency. This factor was tested by exposing glass surfaces modified with the different deposition reaction times to the constant concentration (100 nM) of the entire nucleic acid complex (e.g., surface strands, target strands and reporter strands conjugated to HRP). FIG. 11 graphically demonstrates that a longer reaction time immobilized more silver above the glass surface. FIG. 12 graphically demonstrates the effect of metal enhancement fluorescence (MEF) on the sensor's functionality. Two different scenarios may be observed in this case. In the first scenario, plasmons from active optical molecules will transfer to the silver nano-islands on the tube surface and will stimulate light generation in response. In the second scenario, glass surfaces are covered with a uniform (monolith) silver layer and transferred plasmons, instead of producing light induction, scattered on the silver surface. The effect of the deposition time on signal enchantment may be observed on the surfaces modified by the different silver deposition times (as can be seen in FIG. 11). At the first reaction period, increase in the number of the silver nano-islands increases immobilized DNA concentrations and therefore, sensors light responses (FIGS. 11-12 section 1, 0-4 min), then further silver deposition times will reduce the number of the separate (isolated) nano-islands. Therefore, the increase in the available immobilization surface decreases the MEFs enhancement effect. Such a combination produces a steady-state section (as can be seen in FIG. 12, section 1, min 5-8), where the plasmons scattering effect is compensated by an increase in the concentration of immobilized DNA. Further deposition reaction will decrease silver nano-islands numbers on the tube surface and produce a more monolithic silver layer (FIG. 11, section 2). Such changes will induce plasmon transfers from the light active molecules to the silver surface. However, to stimulate silver layer light activities, plasmons will be scattered on the surface, causing the entire system's light activities to decrease (FIG. 12, section 2).

Finally, to examine the sensitivity of the system to different concentrations of specific mRNA sequence (Cgl_00014454; enoyl-CoA-hydratase/isomerase), before and after the above-described optimization steps (depicted in FIG. 6-12), the modified surfaces of the present invention were exposed to the mixtures with a fixed concentration (100 nM) of the quiescent-stage reporter strand and a fixed concentration (100 nM) of surface strands (immobilized strand), and different concentrations of the target RNA strand from the tested sample. Reference is now made to FIG. 13A graphically depicting the ability of the system of the present invention to distinguish between different concentrations of the target RNA strand molecules in solution up to a 10 nM threshold using the pre-optimization protocol. Reference is now made to FIG. 13B graphically depicting the system's sensitivity after the implementation of the optimized immobilization protocol, described above. As can be seen, implementing the optimization steps increased the system's sensitivity up to concentrations of 3.3 nM (differences were not observed for lower concentrations).

Example 9

The system of the present invention can be used to detect the presence of various fungi strains in postharvest produce, and the developmental stages the fungi are at (appressoria, quiescent and necrotrophic). Initially, there was a need to find target transcripts for each of the tested species (*Botrytis cinerea, Penicillium expansum* and *Alternaria alternata*), which would characterize the different developmental stages of each fungus.

In order to find new target genes that are upregulated during the quiescent stage of several main pathogenic fungi, which heavily impact postharvest crops, mature-unripe (green) and mature ripe (red) tomato fruits were wound-inoculated with conidia of the above-mentioned fungi. Two days and three days after the inoculation of red and green tomato fruit, respectively, the fungi were at necrotrophic and quiescent stages. RNA was extracted from the inoculation area and transcriptome analysis was performed using Next-Seq 500 (Nancy and Stephen Grand Israel National Center, Weizmann Institute of Science, Israel). The resulted sequences of both fruit and fungal transcriptomes were bioinformatically analyzed by introducing the sequences to the Blast tool, comparing them to both fungal and tomato genomes. Serval of the selected fungal genes that were significantly upregulated at the quiescent stage (infection of mature-unripe, green tomato fruit) are presented in FIG. 14. FIG. 14A depicts transcripts upregulated during the quiescent stage of *Alternaria alternata*. FIG. 14B depicts transcripts upregulated during the quiescent stage of *Botrytis cinerea*. FIG. 14C depicts transcripts upregulated during the quiescent stage of *Penicillium expansum*. The sequences of those genes of interest were identified based on each fungal genome sequence.

Figure 15:
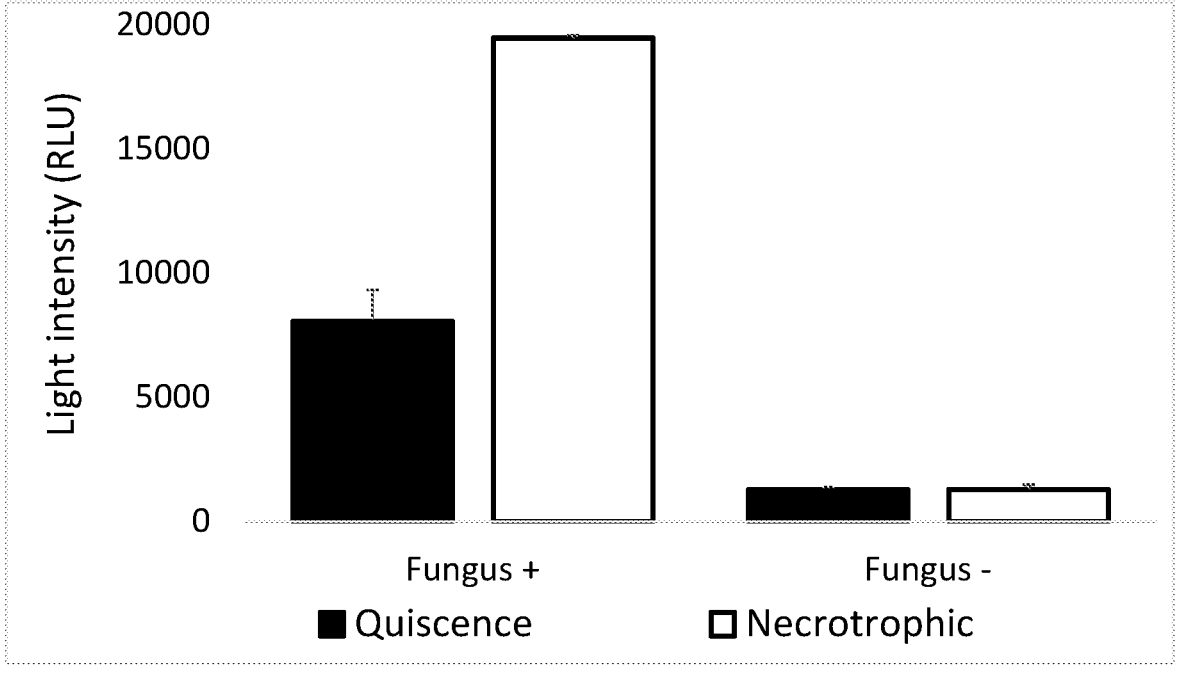
FIG. 15 depicting a graphical presentation of the system's responsiveness to *Botrytis cinerea* at different developmental stages.
Figure 16:
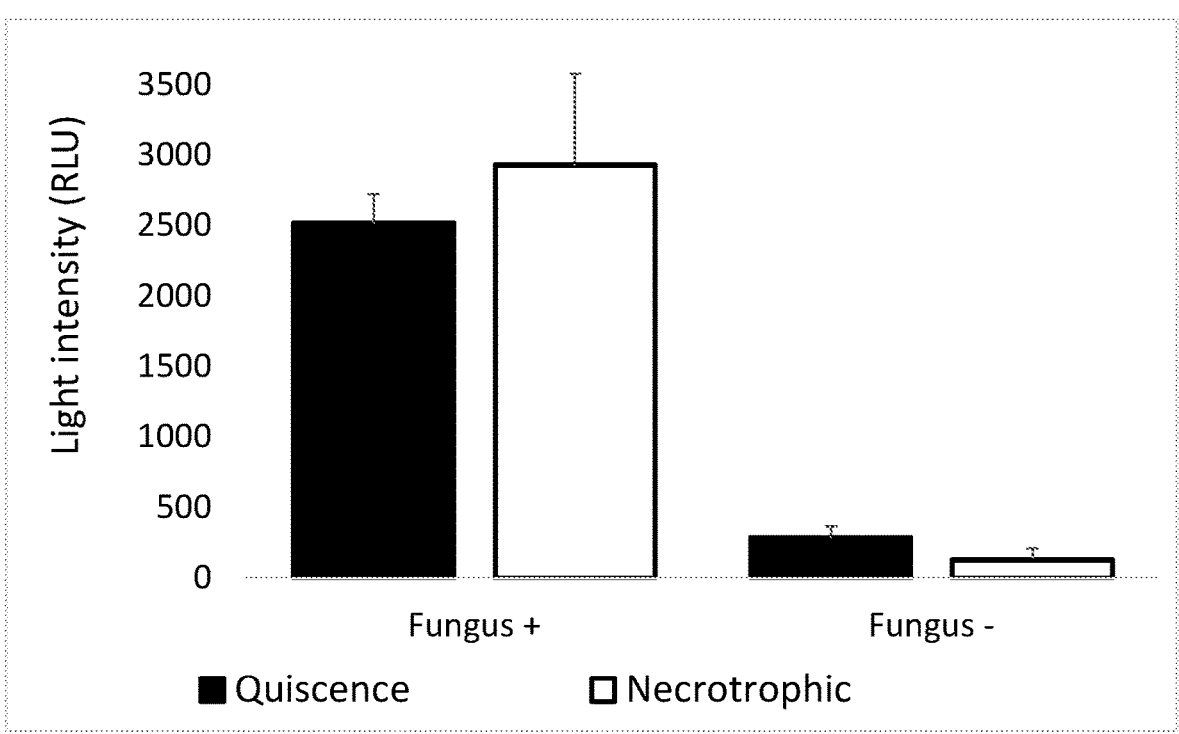
FIG. 16 depicting a graphical presentation of the system's responsiveness to *Alternaria alternata* at different developmental stages.
Figure 17:
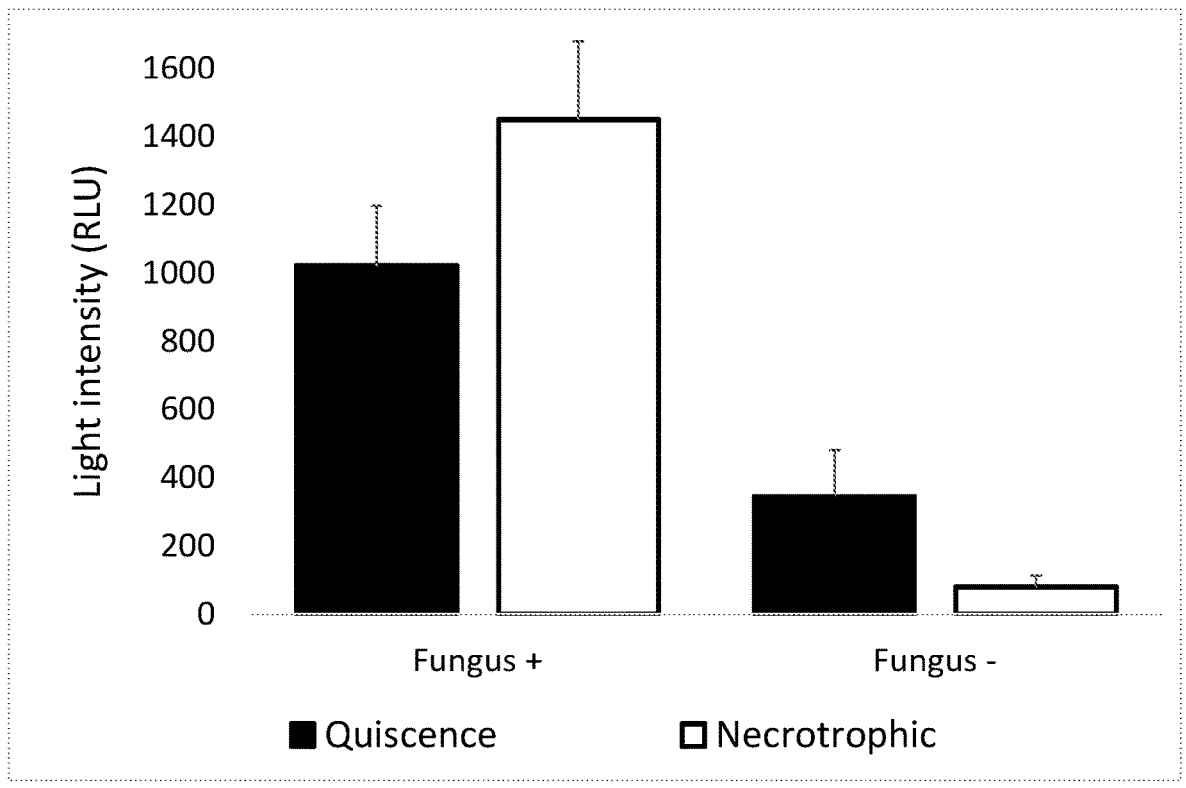
FIG. 17 depicting a graphical presentation of the system's responsiveness to *Penicillium expansum* at different developmental stages.

FIGS. 15-17 graphically illustrate the responses of the system of the present invention to the different fungus strains (*Botrytis cinerea, Alternaria alternata, Penicillium expansum*) at two different in-vivo stages on tomato fruit: quiescence (latent stage) and necrotrophic (pathogenic stage). FIG. 15 depicts the response of the present system to *Botrytis cinerea*, FIG. 16 depicts the response of the present system to *Alternaria alternata* and FIG. 17 depicts the response of the present system to *Penicillium expansum*.

In parallel, the system of the present invention was exposed to the samples without target strands (as a negative control).

Table 1. demonstrates different genes used as specific quiescence markers in different pathogenic fungus strains. During quiescence, mRNA transcription is induced, with more RNA strands hybridizing to the immobilized surface and reporter DNA sequences and therefore, stronger light emission is observed. During active pathogenicity, the fungi will grow and proliferate, leading to similar or different light emissions (depending on the transformation switching progress from quiescence to the necrotrophic stages). If mRNA is extracted from the beginning of both quiescence and necrotrophic stages, the highest differences between sensor response will be observed (i.e., *Botrytis cinerea*, FIG. 15). Similar responses will be observed if mRNA extracts are taken from fungus experiencing the latest quiescence stages and switching to the necrotrophic stages (i.e., *Alternaria alternata*, FIG. 16). Two different parameters may explain the differences in the sensor response in terms of necrotrophic/quiescence ratio. The first is the progression in the fungus transformation from latent to pathogenic stages, which decreases the quiescent mRNA expression and therefore, reduces sensor signal values. The second parameter is the progression in the necrotrophic processes that will reduce mRNA expression and device responses (i.e., *Penicillium expansum*, FIG. 17). These results indicate that the system of the present invention is not only able to determine the presence of the different pathogens in fresh postharvest produce, but also sense fungi at their various pathogenicity stages.

TABLE 1

Genes expressed at quiescence stage and used as markers

| | | Gene analysis | |
| --- | --- | --- | --- |
| Fungi | Gene | log2Fold Change | Padj |
| *Alternaria alternata* | Ferritin ribonucleotide reductase-like protein | 5.920314 | 0.00792900000 |
| *Penicillium expansum* | Glycoside hydrolase, superfamily | 3.458954 | 0.000000000163 |
| *Botrytis cinerea* | Hypothetical protein | 5.769579 | 0.000000794000000000 |

The experiment described above (whose results are shown in FIGS. 15-17) comprises a biosensor, whose surface was made of covalent immobilized streptavidin modified plastic. The immobilized strand was conjugated to biotin, so the linkage between biotin and streptavidin resulted in the immobilization of the strand to the surface of the system. The reporter strand in this experiment was conjugated to the fluorescent fluorophore, fluorescein. The fluorescence emitted from the fluorescein-conjugated reporter strands was detected by the optical photodetector and converted into measurable values.

Example 10

The following sequences represent non-limiting examples of strands that can be incorporated and utilized in the present invention for the detection of fungi during their quiescent stage in postharvest produce:

Reporter strand (SEQ ID NO 1): HRP—5'-TGA GGC GTG GGA AGC AAC-3' with reverse complementarity to the quiescent marker (Cgl_00014454; enoyl-CoA-hydratase/isomerase).

Surface-strand (SEQ ID NO 2): 5'-ATG CAC CGT AGC GAC CAG AG-3'-SH thiolated DNA sequences with conjugated fluorescein isothiocyanate (FITC)—5'-ATG CAC CGT AGC GAC CAG AG-3'-SH). This sequence was used for the evaluation of immobilization efficiency and effect of DTT on the immobilization processes, as depicted in Example 4.

A positive target of the quiescent marker (SEQ ID NO 3): 5'-CCC AAG CTC ATA GGA CTG TCT AAG GCG AGC CAC GTC ACG ACC ACT GGA GAC GTG TAT CCC GTC ACC GAT CCA CTC GTC AAT GGG CTG TTC TCA AAG TTG CTT CCC ACG CCT CAA CAC ACA GTC-3'

Negative target sequences (SEQ ID NO 4, Cgl_00010698; pectate lyase): 5'-TCG TCT TGG GTC TCT GGT CGC TAC GGT GCA TCT CTC ATG CGC TCA GTC TCT GTG AGA CGC GAG TGA ACT TCG TTT TAC TGG TTA AAG AAC GGG GAA GGA AGA CAA CGA ACC ACG ACT ATT TCT-3' and (SEQ ID NO 5, Cgl_00010395; secretory lipase): 5'-TGG AAG TCC GGT CCA TGC TCG CGT GTA TCC TGA TAT GGG ACA CGG CCA GGT TTT GGA GGC CGC CAG GGC TGA TAT CGC TGC TTG GAT CGC CGC GAG ATT TGA AGG AGT TCC CGT TGA GAA GAC-3').

---

The invention claimed is:

1. A system for detecting fungi in a plant tissue, said system comprises:
   a. a measuring transducer;
   b. a surface; and
   c. nucleic acid strands immobilized onto said surface;
wherein said system comes in contact with a mixture comprising:
   (i) target RNA sequences from said fungi; and
   (ii) reporter strands conjugated to a signal-generating component;
wherein said target RNA sequences from said fungi anneal to said nucleic acid strands immobilized onto said surface of said system, further wherein said reporter strands anneal to said target RNA sequences, further wherein said signal-generating component is configured to generate a detectable reaction, further wherein said system is configured to indicate the developmental stage of said fungi,
   further wherein said nucleic acid strands immobilized onto said surface comprise SEQ ID NO 2.

2. The system of claim 1, wherein said fungi are selected from a group consisting of: *Magnaporthe oryzae, Botrytis cinerea, Colletotrichum gloeosporioides, Puccinia* spp, *Fusarium graminearum, Fusarium oxysporum, Blumeria graminis, Mycosphaerella graminicola, Colletotrichum* spp, *Ustilago maydis, Diplodia natalensis, Alternaria alternata, Penicillium digitatum, Penicillium expansum, Pestalotia psidii, Monilinia fructicola, Monilinia laxa, Neonectria ditissima, Rhizopus stolonifer* and *Melampsora lini.*

3. The system of claim 1, wherein said measuring transducer is selected from a group consisting of: optical means selected from a group consisting of CMOS, CCD, PMT, plate readers, cameras and any combination thereof; electrochemical means selected from a group consisting of electrodes, electrode cells, screen-printed electrodes with conductimetric, amperometric, impedimetric or potentiometric components and any combination thereof; acoustic means; thermal means; mass-balance means and any combination thereof.

4. The system of claim 1, wherein said surface is selected from a group consisting of: silica, metal, glass, plastic, organic polymers, non-organic polymers, thiolated particles, nanomaterials, modified silica and any combination thereof.

5. The system of claim 1, wherein said nucleic acid strands immobilized onto said surface are fixed to said surface by immobilization techniques selected from a group consisting of: adsorption, covalent bonding, entrapment, cross-linking, self-assembling, encapsulation and any combination thereof.

6. The system of claim 1, wherein said nucleic acid strands immobilized onto said surface and said reporter strands are selected from a group consisting of: deoxyribonucleic acid, ribonucleic acid, hybridized strand comprising deoxyribonucleic acid and ribonucleic acid and any combination thereof.

7. The system of claim 1, wherein said signal-generating component is selected from a group consisting of: enzymes such as horseradish peroxidase, fluorescence-based molecules, luminescence-based molecules, piezoelectric biosensors, thermometric biosensors, optical biosensors, affinity binding molecules, colorimetric materials and any combination thereof.

8. The system of claim 1, wherein said target RNA sequences are characteristic of different developmental stages in the life cycle of said fungi, said developmental stages being selected from group consisting of: appressoria, quiescence and the necrotrophic stage.

9. The system of claim 1, wherein said target RNA sequences are enoyl-CoA-hydratase/isomerase (SEQ ID NO 3).

10. The system of claim 1, wherein said reporter strands are SEQ ID NO 1, conjugated to horseradish peroxidase at the 5' end.

11. The system of claim 1, wherein said SEQ ID NO 2 comprises fluorescein isothiocyanate at the 5' end and a thiol group at the 3' end.

12. The system of claim 1, wherein said system is configured to detect said target RNA sequences from said fungi at a concentration of about 3.3 nM.

* * * * *